United States Patent
Moore et al.

(10) Patent No.: US 6,632,938 B2
(45) Date of Patent: Oct. 14, 2003

(54) PROCESSES OF PURIFYING OLIGONUCLEOTIDES

(75) Inventors: Max N. Moore, Encinitas, CA (US); John Charles Arthur, San Diego, CA (US); Kent Vansooy, Vista, CA (US); Anthony N. Scozzari, Vista, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/876,242

(22) Filed: Jun. 7, 2001

(65) Prior Publication Data

US 2003/0055241 A1 Mar. 20, 2003

(51) Int. Cl.[7] .................. C07H 21/00; C07H 21/02; C07H 21/04
(52) U.S. Cl. .................. 536/25.4; 536/1.11; 536/22.1; 536/25.3; 536/25.31; 536/27.1
(58) Field of Search .................. 536/22.1, 25.4, 536/25.31, 25.3, 27.1, 24.3, 1.11

(56) References Cited

U.S. PATENT DOCUMENTS

| 5,210,264 A | | 5/1993 | Yau .................. 558/167 |
| 5,304,603 A | * | 4/1994 | Cheng et al. |
| 5,656,741 A | * | 8/1997 | Chow et al. |
| 6,399,765 B1 | * | 6/2002 | Krotz et al. |

OTHER PUBLICATIONS

Beaucage, S. L. et al., "Advances in the Synthesis of Oligonucleotides by the Phosphoramidite Approach," *Tetrahedron*, 1992, 48, 2223–2311.

* cited by examiner

*Primary Examiner*—James O. Wilson
*Assistant Examiner*—Traviss C. McIntosh, III
(74) *Attorney, Agent, or Firm*—Woodcock Washburn LLP

(57) ABSTRACT

Methods for preparing purified oligonucleotides by treating a solution comprising an oligonucleotide with an aggregating agent and a precipitation enhancer under conditions sufficient to form an oligonucleotide aggregate and isolating the oligonucleotide aggregate to produce a purified oligonucleotide.

61 Claims, 5 Drawing Sheets

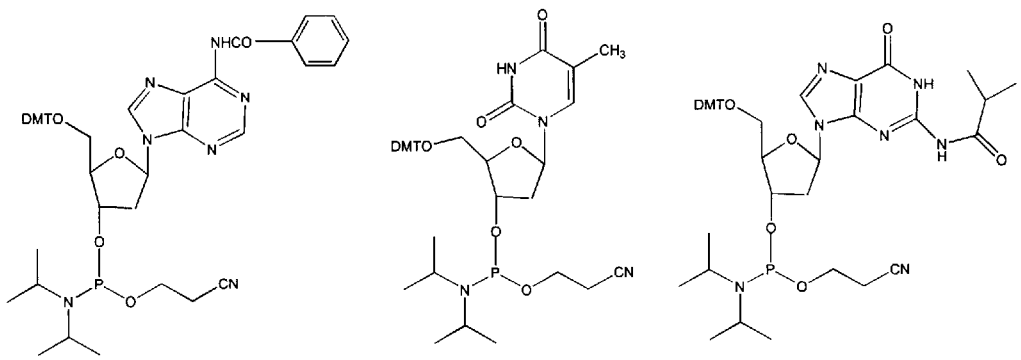

N6-Benzoyl-5'-O-(4,4'-dimethoxytrityl)-2'-deoxyadenosine-3'-(2-cyanoethyl-N,N-diisopropyl)-phosphoramidite 5'-O-(4,4'-dimethoxytrityl)-thymidine-3'-(2-cyanoethyl-N,N-diisopropyl)-phosphoramidite N2-Isobutyryl-5'-O-(4,4'-dimethoxytrityl)-2'-deoxyguanosine-3'-(2-cyanoethyl-N,N-diisopropyl)-phosphoramidite

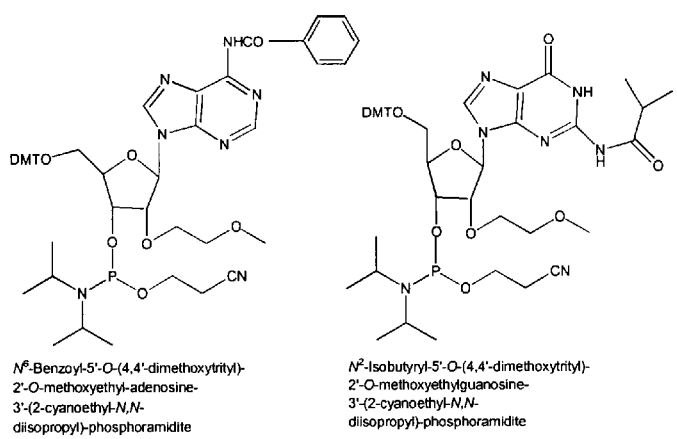

N6-Benzoyl-5'-O-(4,4'-dimethoxytrityl)-2'-O-methoxyethyl-adenosine-3'-(2-cyanoethyl-N,N-diisopropyl)-phosphoramidite N2-Isobutyryl-5'-O-(4,4'-dimethoxytrityl)-2'-O-methoxyethylguanosine-3'-(2-cyanoethyl-N,N-diisopropyl)-phosphoramidite

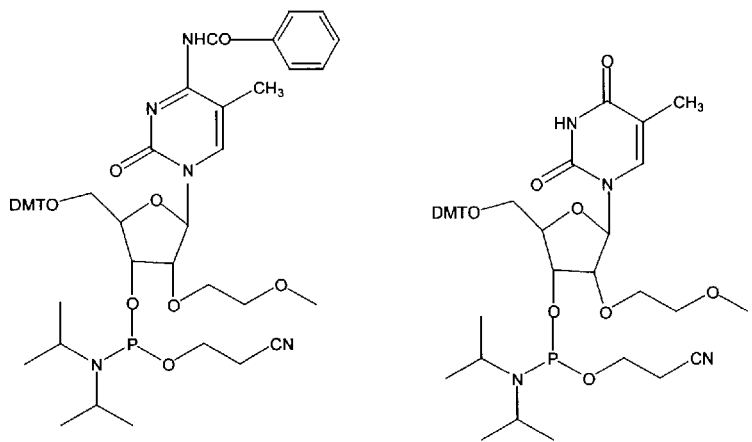

N4-Benzoyl-5'-O-(4,4'-dimethoxytrityl)-2'-O-methoxyethyIc-5-methylcytidine-3'-(2-cyanoethyl-N,N-diisopropyl)-phosphoramidite 5'-O-(4,4'-dimethoxytrityl)-5-methyl uridine-2'-O-methoxyethyl 3'-(2-cyanoethyl-N,N-diisopropyl)-phosphoramidite

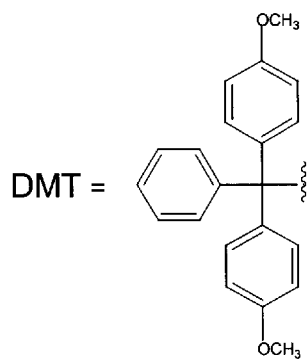

DMT =

Figure 2

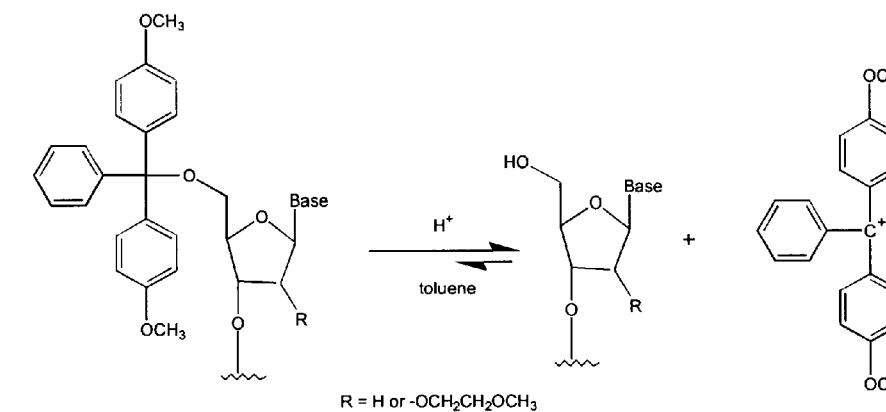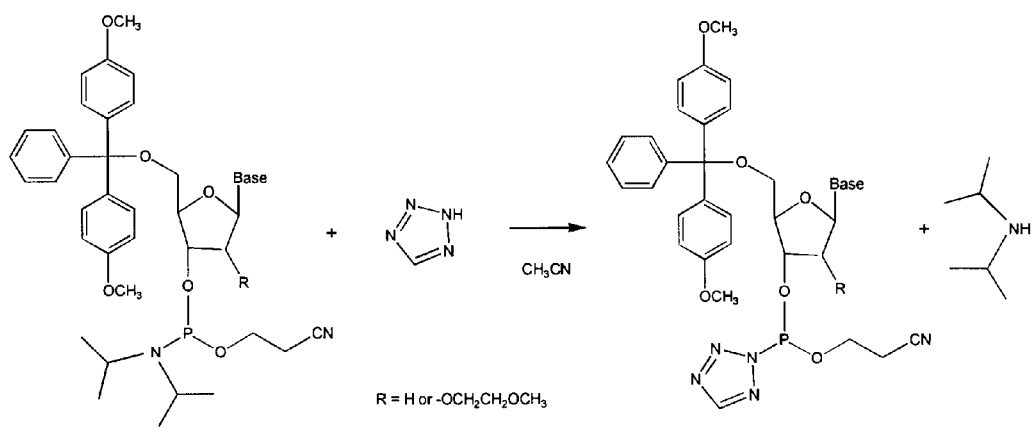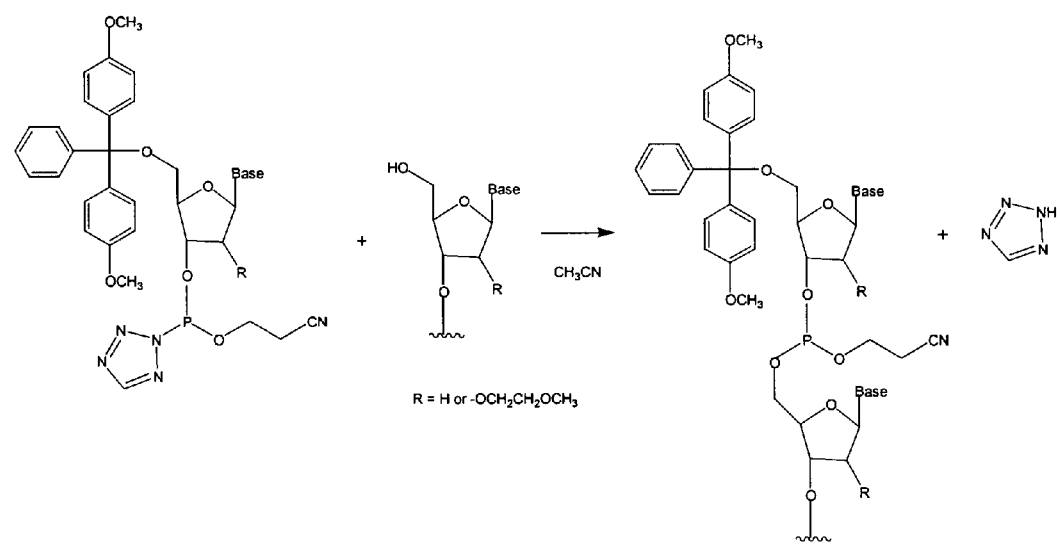
Figure 3

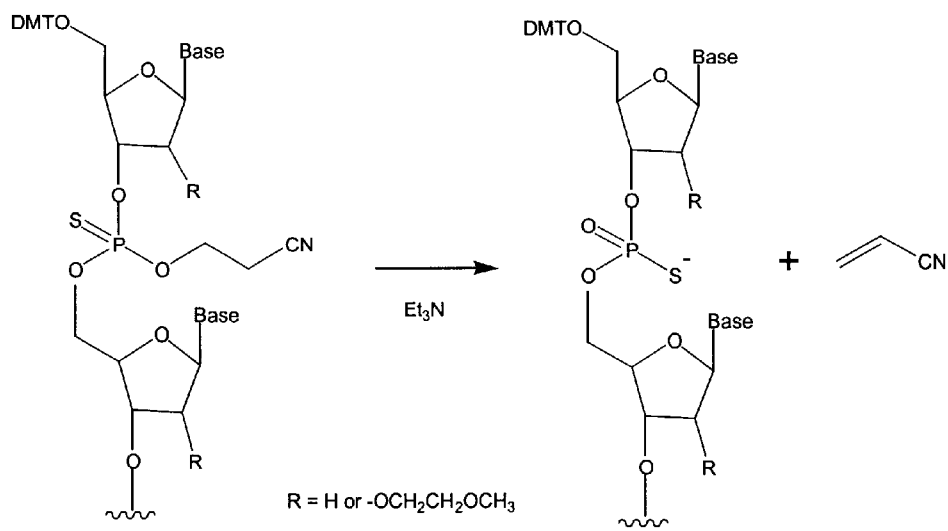
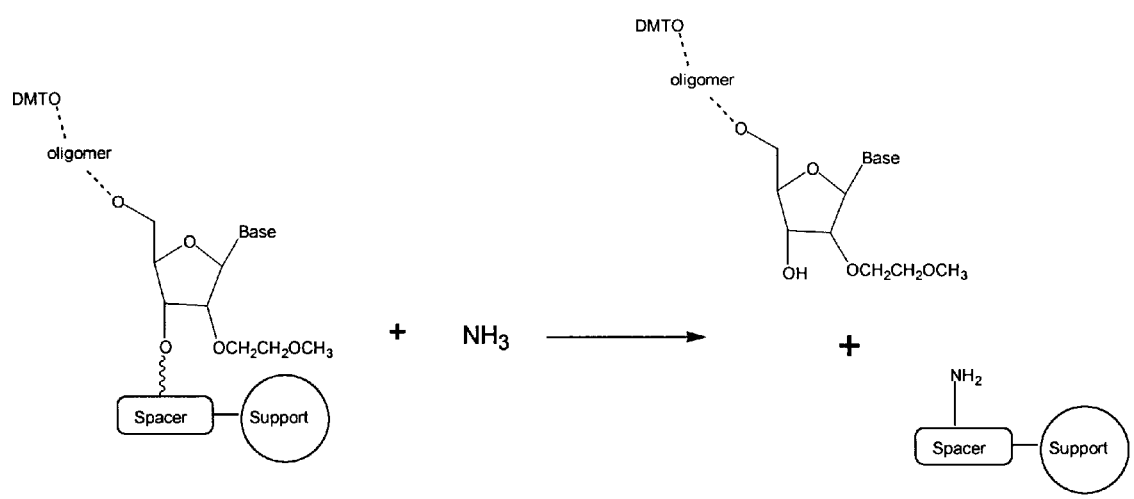
Figure 6

PROCESSES OF PURIFYING OLIGONUCLEOTIDES

FIELD OF THE INVENTION

The present inventions relate to novel methods for purifying oligonucleotides. More specifically, the present inventions relate to novel methods for purifying oligonucleotides wherein the oligonucleotides are precipitated from solution and isolated using physical means.

BACKGROUND OF THE INVENTION

Oligonucleotides and their analogs have been developed and used in molecular biology as probes, primers, linkers, adapters, and gene fragments in a variety of procedures. Oligonucleotides play a significant role, for example, in the fields of therapeutics, diagnostics, and research.

It is well known that most of the bodily states in multicellular organisms, including most disease states, are effected by proteins. Such proteins, either acting directly or through their enzymatic or other functions, contribute in major proportion to many diseases and regulatory functions in animals and humans. For disease states, classical therapeutics has generally focused upon interactions with such proteins in efforts to moderate their disease-causing or disease-potentiating functions. In newer therapeutic approaches, modulation of the actual production of such proteins is desired. By interfering with the production of proteins, the maximum therapeutic effect may be obtained with minimal side effects. It is therefore a general object of such therapeutic approaches to interfere with or otherwise modulate gene expression, which would lead to undesired protein formation.

One method for inhibiting specific gene expression is with the use of oligonucleotides, especially oligonucleotides that are complementary to a specific target messenger RNA (mRNA) sequence. Several oligonucleotides are currently undergoing clinical trials for such use. Phosphorothioate oligonucleotides are presently being used as antisense agents in human clinical trials for various disease states, including use as antiviral agents. Other mechanisms of action have also been proposed. For example, transcription factors interact with double-stranded DNA during regulation of transcription. Oligonucleotides can serve as competitive inhibitors of transcription factors to modulate their action. Several recent reports describe such interactions (see Bielinska, A., et. al., *Science*, 1990, 250, 997–1000; and Wu, H., et. al., *Gene*, 1990, 89, 203–209), incorporated herein by reference in its entirety.

In addition to use as both indirect and direct regulators of proteins, oligonucleotides and their analogs also have found use in diagnostic tests. Such diagnostic tests can be performed using, for example, biological fluids, tissues, intact cells or isolated cellular components. As with gene expression inhibition, diagnostic applications utilize the ability of oligonucleotides and their analogs to hybridize with a complementary strand of nucleic acid. Hybridization is the sequence specific hydrogen bonding of oligomeric compounds via Watson-Crick and/or Hoogsteen base pairs to RNA or DNA. The bases of such base pairs are said to be complementary to one another.

Oligonucleotides and their analogs are also widely used as research reagents. They are useful for understanding the function of many other biological molecules as well as in the preparation of other biological molecules. For example, the use of oligonucleotides and their analogs as primers in PCR reactions has given rise to an expanding commercial industry. PCR has become a mainstay of commercial and research laboratories, and applications of PCR have multiplied. For example, PCR technology now finds use in the fields of forensics, paleontology, evolutionary studies and genetic counseling. Commercialization has led to the development of kits that assist non-molecular biology-trained personnel in applying PCR. Oligonucleotides and their analogs, both natural and synthetic, are employed as primers in such PCR technology.

Oligonucleotides and their analogs are also used in other laboratory procedures. Several of these uses are described in common laboratory manuals such as *Molecular Cloning, A Laboratory Manual*, Second Ed., J. Sambrook, et al., Eds., Cold Spring Harbor Laboratory Press, 1989; and *Current Protocols In Molecular Biology*, F. M. Ausubel, et al., Eds., Current Publications, 1993; each incorporated herein by reference in its entirety. Such uses include, for example, synthetic oligonucleotide probes, screening expression libraries with antibodies and oligomeric compounds, DNA sequencing, in vitro amplification of DNA by the polymerase chain reaction, and in site-directed mutagenesis of cloned DNA. See Book 2 of *Molecular Cloning, A Laboratory Manual*, supra. See also "DNA-protein interactions and The Polymerase Chain Reaction" in Vol. 2 of *Current Protocols In Molecular Biology*, supra; each incorporated herein by reference in its entirety.

Owing to the wide range of applications, oligonucleotides and their analogs have been customized to provide properties that are tailored for desired uses. Thus, a number of chemical modifications have been introduced into oligomeric compounds to increase their usefulness in diagnostics, as research reagents and as therapeutic entities. Such modifications include, but are not limited to, those designed to increase binding to a target strand, to assist in identification of the oligonucleotide or an oligonucleotide-target complex, to increase cell penetration, to stabilize against nucleases and other enzymes that degrade or interfere with the structure or activity of the oligonucleotides and their analogs, to provide a mode of disruption (terminating event) once sequence-specifically bound to a target, to improve the pharmacokinetic properties of the oligonucleotide, and to modulate uptake and cellular distribution of the oligonucleotide.

Modifications to naturally occurring oligonucleotides include, for example, labeling with nonisotopic labels, e.g. fluorescein, biotin, digoxigenin, alkaline phosphatase, or other reporter molecules. Other modifications have been made to the ribose phosphate backbone to increase the nuclease stability of the resulting analog. Examples of such modifications include, but are not limited to, incorporation of methyl phosphonate, phosphorothioate, or phosphorodithioate linkages, and 2'-O-methyl ribose sugar units.

Antisense oligonucleotides also may be modified to conjugate with lipophilic molecules. The presence of the lipophilic conjugate has been shown to improve cellular permeation of the oligonucleotide and, accordingly, improve distribution of the oligonucleotide in cells. Further, oligonucleotides conjugated with lipophilic molecules are able to enhance the free uptake of the oligonucleotides without the need for any transfection agents in cell culture studies. Conjugated oligonucleotides are also able to improve the protein binding of oligonucleotides containing phosphodiester linkages. With the success of these compounds for both diagnostic and therapeutic uses, there exists an ongoing demand for improved oligonucleotides and their analogs.

The chemical literature discloses numerous processes for coupling nucleosides through phosphorous-containing covalent linkages to produce oligonucleotides of defined sequence. One of the most popular processes is the phosphoramidite technique (see, e.g., Advances in the Synthesis of Oligonucleotides by the Phosphoramidite Approach, Beaucage, S. L.; Iyer, R. P., *Tetrahedron*, 1992, 48, 2223–2311 and references cited therein each incorporated herein by reference in its entirety), wherein a nucleoside or oligonucleotide having a free hydroxyl group is reacted with a protected cyanoethyl phosphoramidite monomer in the presence of a weak acid to form a phosphite-linked structure. Oxidation of the phosphite linkage followed by hydrolysis of the cyanoethyl group yields the desired phosphodiester or phosphorothioate linkage.

The ability of the acylaminoethyl group to serve as a protecting group for certain phosphate diesters was first observed by Ziodrou and Schmir. Zioudrou et al., *J. Amer. Chem. Soc.*, 85, 3258, 1963; incorporated herein by reference in its entirety. A version of this method was extended to the solid phase synthesis of oligonucleotide dimers, and oligomers with oxaphospholidine nucleoside building blocks as substitutes for conventional phosphoramidites. Iyer et al., *Tetrahedron Lett.*, 39, 2491–2494, 1998; PCT International Publication WO/9639413, published Dec. 12, 1996; each incorporated herein by reference in its entirety. Similar methods using N-trifluoroacetyl-aminoalkanols as phosphate protecting groups has also been reported by Wilk et al., *J. Org. Chem.*, 62, 6712–6713, 1997; incorporated herein by reference in its entirety. This deprotection is governed by a mechanism that involves removal of an N-trifluoroacetyl group followed by cyclization of aminoalkyl phosphotriesters to azacyclanes, which is accompanied by the release of the phosphodiester group.

Solid phase techniques continue to play a large role in oligonucleotidic synthetic approaches. Typically, the 3'-most nucleoside is anchored to a solid support that is functionalized with hydroxyl or amino residues. The additional nucleosides are subsequently added in a step-wise fashion to form the desired linkages between the 3'-functional group of the incoming nucleoside, and the 5'-hydroxyl group of the support bound nucleoside. Implicit to this step-wise assembly is the judicious choice of suitable phosphorus protecting groups. Such protecting groups serve to shield phosphorus moieties of the nucleoside base portion of the growing oligomer until such time that it is cleaved from the solid support.

After cleavage, the oligonucleotide usually must undergo treatment and processing such as, in some instances, deprotection, precipitation and isolation, in order to produce a purified oligonucleotide product. Precipitation is the process in which an oligonucleotide product in solution is treated with an anti-solvent to form an agglomerated solid in suspension. The solid product is then isolated from the liquid phase. Established methods for precipitation and drying of oligonucleotides have been well documented. Oligonucleotides can be prepared following, for example, the technique described in Maniatis', *Techniques in Molecular Biology*.

One technique for purifying oligonucleotides involves, for example, DMT-on full-length fractions that are isolated by reversed phase HPLC and pooled, precipitated in a large volume of ethanol at −20° C., isolated by continuous flow high-speed centrifugation (15K), and then reconstituted in water. The 4,4'-dimethoxytrityl ether protecting group is removed by acidifying the aqueous oligonucleotide solution to within a range of pH 3.3 to 4.1. After the reaction is complete the solution is diluted with 3 M sodium acetate, then precipitated in ethanol at −20° C., isolated by high-speed centrifugation and reconstituted in water. The aqueous oligonucleotide solution is adjusted to pH 7.0–7.4 with 1 N sodium hydroxide, precipitated in ethanol at −20° C., isolated by continuous flow high speed centrifugation then reconstituted in water. The final reconstituted aqueous oligonucleotide is dried by lyophilization using a 56-hour drying cycle.

However, the above purification scheme requires the use of expensive high-speed centrifuges which are generally only able to process relatively small batches of oligonucleotide. Further, the above method requires large quantities of solvents to be cooled to −20° C.

In light of the foregoing, there is a continued need for improved methods of purifying oligonucleotides. In particular, there is a need for methods of rapidly and efficiently producing a high-yield of purified oligonucleotides. The methods can preferably be performed at ambient temperature. Further, the methods preferably enable the purified oligonucleotides to be separated from solution using cost-effective isolation techniques.

SUMMARY OF THE INVENTION

The present inventions relate to novel methods for purifying oligonucleotides and for producing a high yield of purified oligonucleotide product. More specifically, the present inventions relate to novel methods for aggregating oligonucleotides and isolating the resulting aggregate. The methods of the present invention can be practiced at ambient temperature and allow the aggregates to be isolated using cost-effective physical techniques. The present inventions also relate to cost-effective downstream processing techniques for small- and large-scale operations.

The present inventions relate to methods for purifying an oligonucleotide comprising the steps of reacting the oligonucleotide with an aggregating agent and a precipitation enhancer, under conditions sufficient to form an oligonucleotide aggregate; and isolating the oligonucleotide aggregate to form an isolated oligonucleotide. In certain embodiments, the aggregating agent is an alcohol, such as methanol, ethanol, 1-propanol, isopropyl alcohol or denatured ethanol. In other embodiments, the precipitation enhancer comprises a salt, such as sodium salt ($Na^+$), lithium salt ($Li^+$), ammonium salt ($NH_4^+$), potassium salt ($K^+$), magnesium salt ($Mg^+$), cesium salt ($Cs^+$) or zinc salt ($Zn^+$). For example, the precipitation enhancer can be sodium acetate (NaOAc) or sodium hydroxide (NaOH).

In certain embodiments of the present inventions, the oligonucleotide is a protected oligonucleotide present in a solution. Protective groups include, but are not limited to, trimethoxytrityl, dimethoxytrityl, monomethoxytrityl, 9-phenylxanthen-9-yl, and 9-(p-methoxyphenyl)xanthen-9-yl. The oligonucleotide is preferably present in solution at a concentration of at least about 550 OD/ml, at least about 600 OD/ml, or at least about 650 OD/ml.

In other embodiments of the present inventions, the oligonucleotide is a deprotected oligonucleotide present in a solution. The oligonucleotide is preferably present in solution at a concentration of at least about 2250 OD/ml, between about 2500 OD/ml and about 7500 OD/ml, or between about 4500 OD/ml and about 6500 OD/ml.

Although the oligonucleotide can be treated with the aggregating agent at a wide range of reaction temperatures, the oligonucleotide is preferably treated with said aggregating agent at a temperature between about 15° C. and about 25° C., and more preferably between about 18° C. and about 20° C.

In certain embodiments, the oligonucleotide is treated with said precipitation enhancer prior to treating said oligonucleotide with said aggregating agent. Alternatively, the oligonucleotide can be treated with said aggregating agent prior to treating said oligonucleotide with said precipitation enhancer, or the oligonucleotide can be treated with a mixture of said precipitation enhancer and said aggregating agent.

The oligonucleotide can be present in a solution. When present in a solution, the oligonucleotide is preferably treated with an aggregating agent in a ratio of about 1 part solution to at least about 1.5 parts aggregating agent by volume, more preferably, between about 2 parts and about 4 parts aggregating agent by volume, and even more preferably, between about 2.5 parts and about 4.5 parts aggregating agent by volume.

In certain embodiments, the oligonucleotide is isolated from said solution by high- or low-speed centrifugation. Alternatively, the oligonucleotide can be isolated from said solution by gravitational settling or filtration.

In a preferred embodiment, a purified oligonucleotide is prepared by treating a first solution comprising a 5'-protected oligonucleotide with an aggregating agent under conditions sufficient to form a first oligonucleotide aggregate, isolating the oligonucleotide, and then dissolving the isolated oligonucleotide aggregate to form a second solution. The second solution is treated with a deprotecting reagent, to remove the 5'-protecting groups, with an aggregating agent and a precipitation enhancer under conditions sufficient to form a second oligonucleotide aggregate, which is isolated and dissolved to form a third solution. The third solution is treated with an aggregating agent and a precipitation enhancer under conditions sufficient to form a third oligonucleotide aggregate, which is isolated to provide a purified oligonucleotide.

In an alternate embodiment, a purified oligonucleotide is prepared by treating a first solution comprising an oligonucleotide with an aggregating agent and a precipitation enhancer under conditions sufficient to form a first oligonucleotide aggregate, isolating and dissolving the isolated first oligonucleotide aggregate to form a second solution. The second solution is treated with an aggregating agent and a precipitation enhancer under conditions sufficient to form a second oligonucleotide aggregate and isolated to produce a purified oligonucleotide.

The first solution can be prepared by acidification of HPLC effluent containing a 5'-protected oligonucleotide, wherein the effluent is produced by HPLC purification of a cleaved and base deblocked 5'-protected oligonucleotide.

In other embodiments, the resulting purified oligonucleotide is at least about 90% pure, and more preferably, at least about 98% pure. In some embodiments, the first solution is effluent obtained from high-pressure liquid chromatography of crude oligonucleotide, wherein the high-pressure liquid chromatography is performed using a column loaded with reverse phase media or strong anion exchange resin.

BRIEF DESCRIPTION OF THE FIGURES

FIG. 2 provides examples of phosphoramidites that may be used in the synthetic schemes described in FIG. 1.

FIG. 3 shows dimethoxytrityl deprotection of a support-bound molecule followed by a condensation reaction in which the support-bound molecule reacts with an activated 2'-deoxy or 2'-methoxyethyl modified phosphoramidite monomer.

FIG. 6 shows a capping step in which any unreacted 5'-hydroxyl groups are acetylated by delivery of a mixture of acetic anhydride in acetonitrile and N-methylimidazole in pyridine/acetonitrile. FIG. 6 also shows the final step in which the support is removed by filtration and washing with a mixture of ethanol and water.

DETAILED DESCRIPTION OF THE INVENTION

Figure 1:
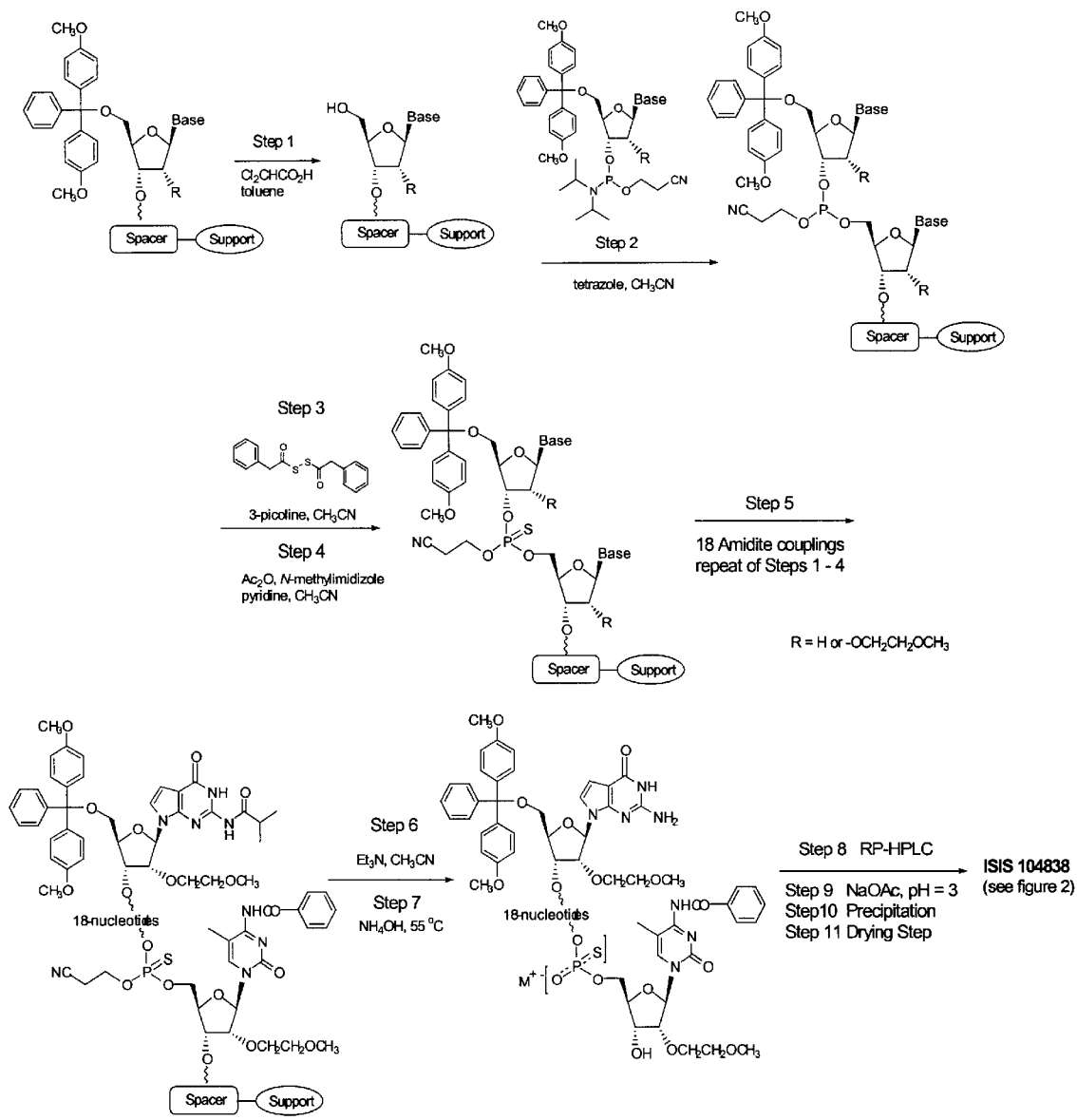
FIG. 1 shows solid phase synthetic schemes for preparing oligonucleotides that may be used in the present inventions.

The present inventions relate to methods for purifying oligonucleotides wherein the oligonucleotide is reacted with at least one aggregating agent and at least one precipitation enhancer, under conditions sufficient to form an oligonucleotide aggregate. The oligonucleotide aggregate is then isolated to provide an isolated oligonucleotide. Due primarily to its size and mass, isolation of the oligonucleotide is facilitated when the oligonucleotide is in aggregate form. For example, an aggregated oligonucleotide is larger and, therefore, more easily isolated by filtration. Likewise, an aggregate is heavier and more susceptible to gravitational influences in a centrifuge or during settling procedures.

By varying reaction conditions such as the aggregating agent used, the precipitation enhancer used, solvent temperature, solvent to oligonucleotide ratio, component order of addition, oligonucleotide concentration and/or solvent type, oligonucleotides can be effectively and efficiently aggregated and subsequently isolated, resulting in purified material. The processes disclosed herein provide a cost-effective alternative to conventional methods of purification because the processes of the present invention can be practiced without the use of equipment such as high-speed centrifuges, chillers and lyophilizers, thereby reducing production time and costs. In addition, by optimizing the reaction conditions in accordance with the present invention, extremely high yields of purified oligonucleotide can be obtained.

The term "oligonucleotide" according to the invention, includes, but is not limited to compounds containing a plurality of monomeric subunits that are joined by phosphorus-containing linkages, such as phosphite, phosphodiester, phosphorothioate, and/or phosphorodithioate linkages. Nuclease resistance may be conferred on the oligonucleotides by utilizing phosphorothioate internucleoside linkages. Oligomeric compounds therefore include oligonucleotides, their analogs, and synthetic oligonucleotides.

As used herein, the term "oligonucleoside" includes oligomers or polymers containing two or more nucleoside subunits having a non-phosphorous linking moiety. Oligonucleosides may have monomeric subunits or nucleosides having a ribofuranose moiety attached to a heterocyclic base moiety through a glycosyl bond.

Oligonucleotides and oligonucleosides can be joined to give a chimeric oligomeric compound. In addition to the naturally occurring phosphodiester linking group, phosphorus and non-phosphorus containing linking groups that can be used to prepare oligonucleotides, oligonucleosides and oligomeric chimeric compounds (oligomeric compounds) include, without limitation, the following:

Phosphorus Containing Linkages:
phosphorodithioate (—O—P(S)(S)—O—);
phosphorothioate (—O—P(S)(O)—O—);
phosphoramidate (—O—P(O)(NJ)—O—);
phosphonate (—O—P(J)(O)—O—);
phosphotriesters (—O—P(O J)(O)—O—);
phophosphoramidate (—O—P(O)(NJ)—S—);
thionoalkylphosphonate (—O—P(S)(J)—O—);
thionoalkylphosphotriester (—O—P(O)(OJ)—S—);
boranophosphate (—R5-P(O)(O)—J—);
Non-phosphorus Containing Linkages:
thiodiester (—O—C(O)—S—);
thionocarbamate (—O—C(O)(NJ)—S—);
siloxane (—O—Si(J)2—O—);
carbamate (—O—C(O)—NH— and —NH—C(O)—O—)
sulfamate (—O—S(O)(O)—N— and —N—S(O)(O)—N—;
morpholino sulfamide (—O—S(O)(N(morpholino)—);
sulfonamide (—O—SO2—NH—);
sulfide (—CH2—S—CH2—);
sulfonate (—O—SO2—CH2—);
N,N'-dimethylhydrazine (—CH2—N(CH3)—N(CH3)—);
thioformacetal (—S—CH2—O—);
formacetal (—O—CH2—O—);
thioketal (—S—C(J)2—O—); and
ketal (—O—C(J)2—O—);
amine (—NH—CH2—CH2—);
hydroxylamine (—CH2—N(J)—O—);
hydroxylimine (—CH=N—O—); and
hydrazinyl (—CH2—N(H)—N(H)—).

"J" denotes a substituent group which is commonly hydrogen or an alkyl group, but which can be a more complicated group that varies from one type of linkage to another.

In addition to linking groups as described above that involve the modification or substitution of one or more of the —O—P(O)2—O— atoms of a naturally occurring linkage, linking groups may include modification of the 5'-methylene group as well as one or more of the atoms of the naturally occurring linkage. Linkages of this type include, without limitation, the following:

amides (—CH2—CH2—N(H)—C(O)) and —CH2—O—N=CH—; and
alkylphosphorus (—C(J)2—P(=O)(OJ)—C(J)2—C(J)2—).
wherein J is as described above.

Synthetic schemes for the synthesis of the substitute internucleoside linkages described above are disclosed in: WO 91/08213; WO 90/15065; WO 91/15500; WO 92/20822; WO 92/20823; WO 91/15500; WO 89/12060; EP 216860; US 92/04294; US 90/03138; US 91/06855; US 92/03385; US 91/03680; U.S. Pat. Nos. 07/990,848; 07/892,902 issued as U.S. Pat. Nos. 5,817,781; 07/806,710; 07/763,130 issued as U.S. Pat. Nos. 5,596,086; 07/690,786; issued as U.S. Pat. Nos. 5,264,562; 5,466,677; 5,034,506; 5,124,047; 5,278,302; 5,321,131; 5,519,126; 4,469,863; 5,455,233; 5,214,134; 5,470,967; 5,434,257; Stirchak, E. P., et al., Nucleic Acid Res., 1989, 17, 6129–6141; Hewitt, J. M., et al., 1992, 11, 1661–1666; Sood, A., et al., J. Am. Chem. Soc., 1990, 112, 9000–9001; Vaseur, J. J. et al., J. Amer. Chem. Soc., 1992, 114, 4006–4007; Musichi, B., et al., J. Org. Chem., 1990, 55, 4231–4233; Reynolds, R. C., et al., J. Org. Chem., 1992, 57, 2983–2985; Mertes, M. P., et al., J. Med. Chem., 1969, 12, 154–157; Mungall, W. S., et al., J. Org. Chem., 1977, 42, 703–706; Stirchak, E. P., et al., J. Org. Chem., 1987, 52, 4202–4206; Coull, J. M., et al., Tet. Lett., 1987, 28, 745; and Wang, H., et al., Tet. Lett., 1991, 32, 7385–7388; incorporated herein by reference in their entirety.

Other modifications can be made to the sugar, to the base, or to the phosphate group of the nucleotide. Representative modifications are disclosed in International Publication Numbers WO 91/10671, published Jul. 25, 1991, WO 92/02258, published Feb. 20, 1992, WO 92/03568, published Mar. 5, 1992, and U.S. Pat. Nos. 5,138,045, 5,218,105, 5,223,618 5,359,044, 5,378,825, 5,386,023, 5,457,191, 5,459,255, 5,489,677, 5,506,351, 5,541,307, 5,543,507, 5,571,902, 5,578,718, 5,587,361, 5,587,469, all assigned to the assignee of this application. The disclosures of each of the above referenced publications are herein incorporated by reference.

As used herein, the term "oligonucleotide analog" means compounds that can contain both naturally-occurring (i.e.

"natural") and non-naturally occurring synthetic moieties, for example, nucleosidic subunits containing modified sugar and/or nucleobase portions. Such oligonucleotide analogs are typically structurally distinguishable from, yet functionally interchangeable with, naturally occurring or synthetic wild type oligo-nucleotides. Thus, oligonucleotide analogs include all such structures that function effectively to mimic the structure and/or function of a desired RNA or DNA strand, for example, by hybridizing to a target. The term "synthetic nucleoside" refers to a modified nucleoside. Representative modifications include modification of a heterocyclic base portion of a nucleoside to give a non-naturally occurring nucleobase, modification of a sugar portion of a nucleoside, and/or modification of an internucleosidic linkage.

As used herein, "unmodified" or "natural" nucleobases include the purine bases adenine and guanine, and the pyrimidine bases thymine, cytosine and uracil. "Modified" or "non-naturally occurring" nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the *Concise Encyclopedia Of Polymer Science And Engineering*, pages 858–859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., Chapter 15, *Antisense Research and Applications*, pages 289–302, Crooke, S. T. and Lebleu, B., ed., CRC Press, 1993; each is incorporated herein by reference in its entirety.

Certain heterocyclic base moieties are particularly useful for increasing the binding affinity of oligomeric compounds to complementary targets. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Id., pages 276–278) and are presently preferred base substitutions, even more particularly when combined with selected 2'-sugar modifications such as 2'-methoxyethyl groups.

Representative United States patents that teach the preparation of heterocyclic base moieties (modified nucleobases) include, but are not limited to, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; and 5,808,027, certain of which are commonly owned, and each of which is herein incorporated by reference in its entirety.

As used herein, the term "2'-substituent group" refers to groups that are attached to select sugar moieties at the 2'-position. However, substituent groups can alternatively or additionally be attached to other positions of the sugar moieties (e.g., the 3'- and/or 5'-positions), selected heterocyclic base moieties, or at both the heterocyclic base and the sugar moiety.

A representative list of substituent groups includes hydrogen, hydroxyl, $C_1$–$C_{20}$ alkyl, $C_2$–$C_{20}$ alkenyl, $C_2$–$C_{20}$ alkynyl, $C_5$–$C_{20}$ aryl, O-alkyl, O-alkenyl, O-alkynyl, O-alky O-alkylalkoxy, O-alkylaminoalkyl, O-alkylimidazole, S-alkyl, S-alkenyl, S-alkynyl, NH-alkyl, NH-alkenyl, NH-alkynyl, N-dialkyl, O-aryl, S-aryl, NH-aryl, O-aralkyl, S-aralkyl, NH-aralkyl, N-phthalimido, halogen (particularly fluoro), amino, thiol, keto, carboxyl, nitro, nitroso, nitrile, trifluoromethyl, trifluoromethoxy, imidazole, azido, hydrazino, hydroxylamino, isocyanato, sulfoxide, sulfone, sulfide, disulfide, silyl, aryl, heterocycle, carbocycle, intercalators, reporter groups, conjugates, polyamine, polyamide, polyalkylene glycol, and polyethers of the formula (O-alkyl)$_m$, where m is 1 to about 10. Preferred among these polyethers are linear and cyclic polyethylene glycols (PEGs), and (PEG)-containing groups, such as crown ethers and those which are disclosed by Ouchi et al. (*Drug Design and Discovery* 1992, 9, 93), Ravasio et al. (*J. Org. Chem.* 1991, 56, 4329) and Delgardo et. al. (*Critical Reviews in Therapeutic Drug Carrier Systems* 1992, 9, 249), each of which is herein incorporated by reference in its entirety. Further sugar modifications are disclosed in Cook, P. D., *Anti-Cancer Drug Design*, 1991, 6, 585–607, incorporated herein by reference in its entirety. Fluoro, O-alkyl, O-alkylamino, O-alkyl imidazole, O-alkylaminoalkyl, and alkyl amino substitution is described in U.S. Pat. No. 6,166,197, hereby incorporated by reference in its entirety.

The oligomeric compounds comprise a plurality of linked nucleosides wherein the preferred internucleoside linkage is a 3',5'-linkage. Alternatively, however, 2',5'-linkages can be used (as described in U.S. application Ser. No. 09/115,043, filed Jul. 14, 1998). A 2',5'-linkage is one that covalently connects the 2'-position of the sugar portion of one nucleotide subunit with the 5'-position of the sugar portion of an adjacent nucleotide subunit.

The oligonucleotides described herein may have asymmetric centers. Unless otherwise indicated, all chiral, diastereomeric, and racemic forms are included in the present invention. Geometric isomers may also be present in the compounds described herein, and all such stable isomers are contemplated by the present invention. It will be appreciated that compounds that contain asymmetrically substituted carbon atoms may be isolated in optically active or racemic forms or by synthesis.

All isotopes of atoms occurring in the intermediates or final compounds are included. Isotopes include those atoms having the same atomic number but different mass numbers. By way of example, and without limitation, isotopes of hydrogen include tritium and deuterium.

Some representative modified oligomeric compounds contain, at least one nucleoside having one of the following substituent groups: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligomeric compound, or a group for improving the pharmacodynamic properties of an oligomeric compound, and other substituents having similar properties. A preferred modification includes 2'-methoxyethoxy [2'-O—$CH_2CH_2OCH_3$, also known as 2'-O-(2-methoxyethyl) or 2'-MOE] (Martin et al., *Helv. Chim. Acta*, 1995, 78, 486), i.e., an alkoxyalkoxy group. A further preferred modification is 2'-dimethylaminooxyethoxy, i.e., a $O(CH_2)_2ON(CH_3)_2$ group, also known as 2'-DMAOE. Representative aminooxy substituent groups are described in co-owned U.S. patent application Ser. No. 09/344,260, filed Jun. 25, 1999, entitled "Aminooxy-Functionalized Oligomers"; and U.S. patent application Ser. No. 09/370,541, filed Aug. 9, 1999, entitled "Aminooxy-Functionalized Oligomers and Methods for Making Same;" hereby incorporated by reference in their entirety.

Other preferred modifications include 2'-methoxy (2'-O—$CH_3$), 2'-aminopropoxy (2'-$OCH_2CH_2CH_2NH_2$) and 2'-fluoro (2'-F). Similar modifications may also be made at other positions on nucleosides and oligomers, particularly the 3' position of the sugar on the 3' terminal nucleoside or at a 3'-position of a nucleoside that has a linkage from the 2'-position such as a 2'–5' linked oligomer and at the 5' position of a 5' terminal nucleoside. Oligomers may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920, certain of which are commonly owned, and each of which is herein incorporated by reference, and commonly owned U.S. patent application Ser. No. 08/468,037, filed on Jun. 5, 1995, now U.S. Pat. No. 5,859,221, also herein incorporated by reference.

The oligomeric compounds in accordance with the invention can be used in diagnostics, therapeutics and as research reagents and kits. They can be used in pharmaceutical compositions by including a suitable pharmaceutically acceptable diluent or carrier. They further can be used for treating organisms having a disease characterized by the undesired production of a protein. The organism should be contacted with an oligonucleotide having a sequence that is capable of specifically hybridizing with a strand of nucleic acid coding for the undesirable protein. Treatments of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, all plants and all higher animal forms, including warm-blooded animals, can be treated. Further, each cell of multicellular eukaryotes can be treated, as they include both DNA-RNA transcription and RNA-protein translation as integral parts of their cellular activity. Furthermore, many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligonucleotides.

The reactions of the synthetic methods claimed herein are carried out in suitable solvents which may be readily understood by those skilled in the art of organic synthesis, the suitable solvents generally being any solvent which is substantially nonreactive with the starting materials (reactants), the intermediates, or products at the temperatures at which the reactions are carried out, i.e., temperatures may range from the solvent's freezing temperature to the solvent's boiling temperature. A given reaction may be carried out in one solvent or a mixture of more than one solvent. Depending on the particular reaction step, suitable solvents for a particular reaction step may be selected.

Methods for assembling oligomers in accordance with the present invention include both solution phase and solid phase chemistries. Representative solution phase techniques are described in U.S. Pat. No. 5,210,264, which is assigned to the assignee of the present invention, and is incorporated by reference herein in its entirety. Representative solid phase techniques are those typically employed for DNA and RNA synthesis utilizing standard phosphoramidite chemistry, (see, e.g., Protocols For Oligonucleotides And Analogs, Agrawal, S., ed., Humana Press, Totowa, N.J., 1993, hereby incorporated by reference in its entirety).

Solid supports according to the invention include those generally known in the art to be suitable for use in solid phase methodologies, including, for example, controlled pore glass (CPG), oxalyl-controlled pore glass (see, e.g., Alul, et al., *Nucleic Acids Research* 1991, 19, 1527, hereby incorporated by reference in its entirety), TentaGel Support—an aminopolyethyleneglycol derivatized support (see, e.g., Wright, et al, *Tetrahedron Letters* 1993, 34, 3373, hereby incorporated by reference in its entirety) and Poros—a copolymer of polystyrene/divinylbenzene Using one particular synthetic scheme, solid phase synthesis utilizes phosphoramidites as activated phosphate compounds. In this technique, a phosphoramidite monomer is reacted with a free hydroxyl on the growing oligomer chain to produce an intermediate phosphite compound, which is subsequently oxidized to the $P^V$ state using standard methods. This technique is commonly used for the synthesis of several types of linkages including phosphodiester, phosphorothioate, and phosphorodithioate linkages.

Typically, the first step in such a process is attachment of a first monomer or higher order subunit to a solid support using standard methods and procedures known in the art. Solid supports are substrates which are capable of serving as the solid phase in solid phase synthetic methodologies, such as those described in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069. A linker is optionally positioned between the terminal nucleotide and the solid support. Linkers are known in the art as short molecules that serve to connect a solid support to functional groups (e.g., hydroxyl groups) of initial synthon molecules in solid phase synthetic techniques. Suitable linkers are disclosed in, for example, *Oligonucleotides And Analogues A Practical Approach*, Ekstein, F. Ed., IRL Press, N.Y, 1991, Chapter 1, pages 1–23, hereby incorporated by reference in its entirety.

The support-bound monomer or higher order synthon is then treated to remove the protecting group from the free terminal end. Typically, this is accomplished by treatment with acid. The solid support bound monomer, or higher order oligomer, is then reacted with individual monomeric or higher order building blocks (i.e., synthons) to form a compound which has a phosphite or thiophosphite linkage. In preferred embodiments, the synthons reacted under anhydrous conditions in the presence of an activating agent such as, for example, 1H-tetrazole, 5-(4-nitrophenyl)-1H-tetrazole, or diisopropylamino tetrazolide.

The present invention can be practiced with protected and unprotected oligonucleotides. "Protected oligonucleotides" refer to oligonucleotides wherein potentially reactive groups on an oligonucleotide are modified by reversible chemical modification. The terms "protective group" and "protecting group" are used herein to include, but not to be limited to, trimethoxytrityl, dimethoxytrityl, monomethoxytrityl, 9-phenylxanthen-9-yl, and 9-(p-methoxyphenyl)xanthen-9-yl tert-butoxycarbonyl, benzyloxycarbonyl, mesityl (2,4,6-trimethylbenzoyl) ester, benzoyl ester, tert-butyldiphenylsilyl ether, triphenylmethyl (trityl; Tr), S-tert-butyl, S-p-butyl, S-p-nitrobenzyl, and S-p-methoxy-benzyl, and phthalimido groups (see e.g., Greene and Wuts, Protective Groups in Organic Synthesis, $2^{nd}$ edition, John Wiley & Sons, New York, 1991), incorporated herein by reference in its entirety.

The oligonucleotide is optionally present in solution. Suitable solvents would be readily understood by those skilled in the art to include any solvent that is substantially nonreactive with the reagents, intermediates, or products at the reaction temperature used. Although any of a variety of solvents can be used, the solvent preferably also functions as the aggregating agent, as discussed below. The concentration of oligonucleotide in solution can vary over a considerable range. For example, oligonucleotide concentrations of between about 550 OD/mL and about 4750 OD/mL can be used. It will be appreciated, however, that the concentration of oligonucleotide in solution could depend on a variety of factors, including the solvent used, and the nature of the oligonucleotide. In particular, when purifying a protected oligonucleotide in solution, the concentration of oligonucleotide present in solution is preferably at least 550 OD/mL, more preferably at least about 600 OD/mL, even more preferably at least about 700 OD/mL, and still more preferably at least about 850 OD/mL. When the oligonucleotide is a deprotected oligonucleotide present in a solution, the oligonucleotide is preferably present in said solution at a concentration of at least about 2250 OD/mL, more preferably at least about 2500 OD/mL, preferably at least about 3000 OD/mL, more preferably at least about 4500 OD/mL, even more preferably at least about 6500 OD/mL, and still more preferably at least about 7500 OD/mL.

The term "OD/mL", as used herein, refers to absorbency at 260 nm and a 1 cm path length as measured using an ultraviolet (UV) spectrophotometer.

The term "aggregating agent" according to the invention, includes, but is not limited to moieties that may be used to treat an oligonucleotide, either directly or when the oligonucleotide is present in solution, and result in the formation of aggregates or solids. Aggregating agents suitable for use with the present invention include, but are not limited to, alcohols such as methanol, ethanol, 1-propanol, isopropyl alcohol and denatured ethanol.

The terms "oligonucleotide aggregate" and "aggregate," as used herein, refer to clusters of oligonucleotides having a size and mass such that they can be subject to isolation by physical means. Physical means for isolating the oligonucleotide aggregates include, but are not limited to, centrifugation, gravitational settling and filtration.

As used herein, the term "precipitation enhancer" refers to species that impart a beneficial effect on precipitation. In one embodiment, the precipitation enhancer comprises a salt. Salts suitable for use as precipitation enhancers include, but are not limited to, sodium salts ($Na^+$), lithium salts ($Li^+$), ammonium salts ($NH_4^+$), potassium salts ($K^+$), magnesium salts ($Mg^+$), cesium salts ($Cs^+$) and zinc salts ($Zn^+$). Particular examples of useful sodium salts include sodium acetate (NaOAc) and sodium hydroxide (NaOH).

The oligonucleotide is reacted with the aggregating agent and the precipitation enhancer under conditions sufficient to form the oligonucleotide aggregate. The resulting purified oligonucleotide product is at least about 90% pure, and more preferably, at least about 98% pure. The percent purity of a resulting oligonucleotide is determined using techniques known to those of ordinary skill in the art, such as, by capillary gel electrophoresis or mass spectroscopy.

The temperature of the reagents (i.e., oligonucleotide, aggregating agent, precipitation enhancer, and/or solvent), the order of addition of reagents, and the ratio of oligonucleotide concentration to aggregating agent concentration can each be individually selected to optimize the formation of oligonucleotide aggregates.

The temperature of the reagents can be varied over a broad range. For example, one or more of the reagents can be chilled. However, sufficiently high yields of isolated oligonucleotides can be obtained with the present invention even when the reagents are used at ambient- or room-temperature. Accordingly, to avoid the use of expensive chillers and their associated time constraints, the reagents are preferably used at room temperature (preferably about 15° C. to about 25° C., and more preferably about 18° C. to about 20° C.).

In addition, the order in which the reagents are mixed can be varied. Specifically, the reagents can be mixed as follows: (a) the oligonucleotide can be treated with the precipitation enhancer prior to treatment with the aggregating agent; (b) the oligonucleotide can be treated with the aggregating agent prior to treatment with the precipitation enhancer; and (c) the oligonucleotide can be treated with a mixture of the precipitation enhancer and the aggregating agent. Preferably, the oligonucleotide is treated with the precipitation enhancer prior to treatment with aggregating agent.

The ratio of oligonucleotide concentration to aggregating agent concentration can also be varied. For example, when the oligonucleotide is in solution, the ratio of oligonucleotide solution to aggregating agent is preferably 1 part solution to at least about 1.5 parts, more preferably at least about 2 part, and even more preferably at least about 2.5 parts aggregating agent by volume. Although ratios of solution to aggregating agent in excess of about 1:2.5 can be utilized, the ratio is preferably maintained at 1 part solution to below about 4.5 parts aggregating agent, and more preferably to below about 4 parts aggregating agent, because the cost of using more aggregating agent does not outweigh the benefits obtained.

Once the oligonucleotide aggregate has been formed, the oligonucleotide aggregate is isolated to provide the isolated oligonucleotide. Due to the size and mass of the oligonucleotide aggregates, physical means for isolating the oligonucleotide aggregates can be beneficially employed. For example, the oligonucleotide can be isolated from solution by high-speed centrifugation, low-speed (e.g., preferably less than about 3000, and more preferably less than about 2500 rotations per minute) centrifugation, gravitational settling, and/or filtration.

The particular isolation method used may influence, at least to some degree, the selection of other reaction conditions (e.g., aggregating agent used and/or ratio of oligonucleotide solution to aggregating agent concentration). For example, when centrifugation or gravitational settling is to be used, the oligonucleotide is preferably treated with an aggregating agent in a ratio of 1 part oligonucleotide to about 5 parts aggregating agent by volume. More specifically, when centrifugation is to be used to isolate an oligonucleotide that has been treated with ethanol, the ratio of oligonucleotide solution to aggregating agent is preferably 1 part oligonucleotide solution to between about 2 and about 4 parts aggregating agent by volume. Likewise, when centrifugation is to be used to isolate an oligonucleotide that has been treated with 1-propanol, isopropyl alcohol and/or denatured ethanol, the ratio of oligonucleotide solution to aggregating agent is preferably 1 part oligonucleotide to about 3 parts aggregating agent by volume. When gravitational settling is to be used to isolate an oligonucleotide that has been treated with ethanol, the ratio of oligonucleotide solution to aggregating agent is preferably 1 part oligonucleotide to between about 2 and about 4.5 parts aggregating agent by volume. Further, when gravitational settling is to be used to treat an oligonucleotide with 1-propanol, isopropyl alcohol and/or denatured ethanol, the of oligonucleotide solution to aggregating agent is preferably 1 part oligonucleotide to about 3 parts aggregating agent by volume.

It will be appreciated that the methods of the present invention can be utilized as part of an oligonucleotide preparation and/or treatment procedure. Accordingly, the methods of the present invention can be used in conjunction with a variety of pre- and/or post-processing steps. For example, the oligonucleotide may be protected, deprotected, and/or reconstituted prior to reacting the oligonucleotide with the aggregating agent and the precipitation enhancer. In addition, the isolated oligonucleotide can be reconstituted prior to further use. Further, it will be appreciated that multiple precipitation steps can be utilized sequentially.

It is intended that each of the patents, applications, printed publications, and other published documents mentioned or referred to in this specification be herein incorporated by reference in their entirety.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

EXAMPLES

The efficacy of the methods of the present invention are illustrated in the following examples. In particular, the examples show the effects of varying factors that influence precipitation properties of oligonucleotides, including solvent temperature, solvent to oligonucleotide ratio, component order of addition, oligonucleotide concentration and solvent type.

Solvents used for precipitation of oligonucleotides were ethanol, ethanol denatured with 5% methanol, 1-propanol and isopropanol (IPA). 3.0 M NaOAc was used to induce phase change during precipitation of DMT-off oligonucleotides. The examples were obtained using oligonucleotides that varied in sequence, purine to pyrimidine ratios, and chemical modifications. The oligonucleotides used are described in Table 1. For example, Oligonucleotide 6 <SEQ ID NO: 6>(ISIS 104838) is a 2'-O-(2-methoxyethyl) modified phosphorothioate oligonucleotide containing a 10-base 2'-deoxy gap, also referred to as a 5-10-5 MOE gapmer. The method used to manufacture Oligonucleotide 6 (ISIS 104838) was a multi-step process that utilized solid phase organic synthesis, preparative reversed phase chromatographic purification, acidic deprotection, solid-liquid separation and vacuum drying to produce the drug substance.

TABLE 1

| Oligonucleotide No. | ISIS No. | Sequence |
|---|---|---|
| 1 | 5132 | <SEQ. ID NO.1> TCCCGCCTGTGACATGCATT |
| 2 | 2302 | <SEQ. ID NO.2> GCCCAAGCTGGCATCCGTCA |
| 3 | 14803 | <SEQ. ID NO.3> GTGCTCATGGTGCACGGTC |
| 4 | 2503 | <SEQ. ID NO.4> TCCGTCATCGCTCCTCAGGG |
| 5 | 3521 | <SEQ. ID NO.5> GTTCTCGCTGGTGAGTTTCA |
| 6 | 104838 | <SEQ. ID NO.6> GCTGATTAGAGAGAGGTCCC |
| 7 | 107248 | <SEQ. ID NO.7> CTGAGTCTGTTTTCCATTCT |
| 8 | 113715 | <SEQ. ID NO.8> GCTCCTTCCACTGATCCTGC |

The chemical synthesis of Oligonucleotide 6 (ISIS 104838) utilized phosphoramidite chemistry and involved sequential coupling of activated monomers to an elongating polymer, one terminus of which was covalently attached to the solid-support matrix. The solid phase approach allowed for easy purification of reaction products at each step in the synthesis by simple solvent washing of the solid-support. Synthesis of the 20-mer was carried out in a sealed reactor without isolation of intermediate oligonucleotides. The chemical synthesis process delivered specified volumes of reagents and solvents to and from the solid-phase chemical reactor. Valves and pumps under computer control regulated the flow of the reagents and solvents.

FIG. 1 shows an oligonucleotide that was sequentially assembled from the 3' end towards the 5' end. The oligonucleotide was assembled by deprotecting the 5' end of the support-bound molecule with dichloroacetic acid in toluene (Step 1), allowing the support-bound molecule to condense with an incoming activated phosphoramidite monomer (Step 2), oxidatively sulfurizing the resulting phosphite triester to a thiophosphate triester (Step 3), and capping any unreacted hydroxyl groups by acylation to prevent non-sequential coupling with the next incoming monomer (Step 4). This series of steps was repeated for subsequent coupling reactions (Step 5). The O-cyanoethyl protecting group was removed (Step 6) and then Oligonucleotide 6 (ISIS 104838) cleaved from the solid support along with concurrent exocyclic amine deprotection (Step 7). The final processing involved preparative reversed phase HPLC (Step 8), acidic deprotection of the 5'-O-4,4'-dimethoxytrityl ether (Step 9), product isolation (Step 10) and vacuum drying of the drug substance (Step 11).

FIGS. 3 through 6 illustrate the manufacturing scheme, in which the synthesis reactions (Steps 1–4) were repeated using the appropriate phosphoramidite to synthesize the drug substance. Examples of phosphoramidites that may be used in this process are shown in FIG. 2.

FIG. 3 describes the dimethoxytrityl deprotection step (Step 1 of FIG. 1), wherein the 5'-O-dimethoxytrityl group was removed, first from the 2'-methoxyethyl ribonucleoside, then subsequently from a 2'-deoxy or 2'-methoxyethylribo nucleotide oligomer, dependent on the progress of the chemical synthesis, by treatment with a 10% v/v solution of dichloroacetic acid (DCA) in toluene. This gives the partially protected support-bound molecule and the relatively stable carbocation. The excess acid and released dimethoxytrityl carbocation were then removed by an acetonitrile wash.

The second step in a complete cycle was a condensation reaction between the newly liberated 5'-hydroxyl of the support bound molecule and an activated 2'-deoxy or 2'-methoxyethyl modified phosphoramidite monomer (Step 2 of FIG. 1). Activation is achieved in situ by mixing an acetonitrile solution of phosphoramidite with an excess of the weak acid 1-H-terazole. The formed tetrazolide reacts quickly with the 5'-hydroxyl group of the support-bound molecule to give phosphite triester and an equivalent of 1-H-tetrazole in near quantitative yield. Excess reagents and by-products are removed from the column reactor by washing with acetonitrile.

Figure 4:
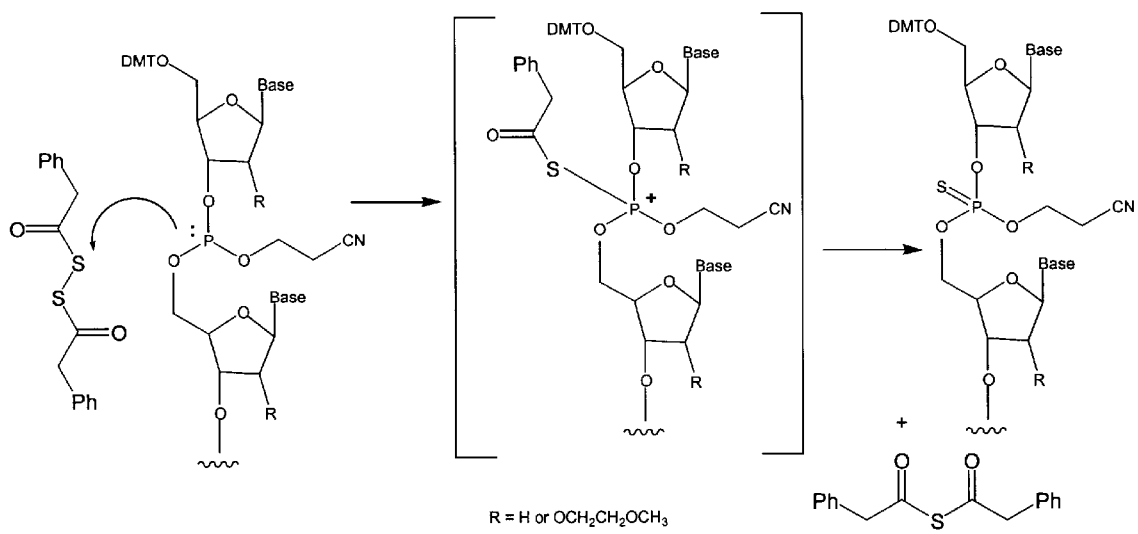
FIG. 4 shows the reaction between a tetrazole and the 5'-hydroxyl group of the support-bound molecule to produce a phosphite triester and an equivalent of 1-H-tetrazole.

FIG. 4 describes sulfurization of phosphite triester by delivering a 0.2 M solution of phenylacetyl disulfide (PADS) in a 1:1 mixture of acetonitrile:3-picoline to the reaction column. This results in the formation of the corresponding phosphorothioate triester. The excess reagent and by-products are removed by washing the support-bound material with acetonitrile.

Figure 5:
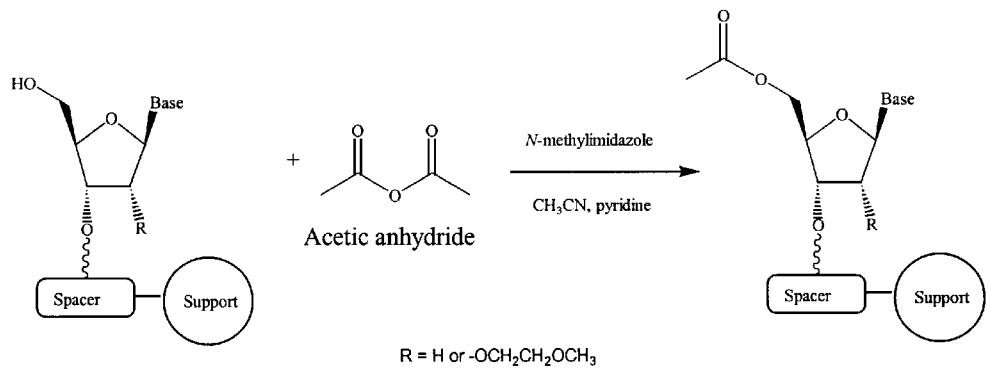
FIG. 5 shows the sulfurization of a phosphite triester by delivering to the reaction column, 0.2 M solution phenylacetyl disulfide (PADS) in a 1:1 mixture of acetonitrile: 3-picoline, which results in the formation of the corresponding phosphorothioate triester.

FIG. 5 describes the final reaction in any given cycle, which was a capping step in which any unreacted 5'-hydroxyl groups are acetylated by delivery of a mixture of acetic anhydride in acetonitrile and N-methylimidazole in pyridine/acetonitrile. The resulting 5'-O-acetates were stable throughout the remainder of the synthesis until cleaved during the final ammonolysis. Excess reagent was removed by an acetonitrile wash.

After nineteen sequential cycles of 5'-hydroxyl deprotection, coupling, sulfurization, and capping, FIG. 6 shows that the cyanoethyl protecting group was removed from the internucleotide linkages by treatment with triethylamine in acetonitrile to produce the phosphorothioate diester while the oligonucleotide was still bound to solid support. This allowed for removal of acrylonitrile generated during the base-mediated β-elimination. Under these conditions, the acrylonitrile generated does not react with thymidine residues present and was simply washed away from the support-bound material. Cleavage and base deprotection were then completed by incubation with ammonium hydroxide at elevated temperature. The support was removed by filtration and washed with a mixture of ethanol and water. The combined filtrate and washings were concentrated and crude, 5'-DMT protected Oligonucleotide 6 (ISIS 104838) was purified by reversed phase (RP)HPLC.

In one method for preparing a purified oligonucleotide, chromatographic purification of the crude, 5'-protected product was accomplished by RP-HPLC. The RP-HPLC step removed DMT-off failure sequences generated as a result of incomplete monomer coupling (Step 2). The process was effective in separating the full-length DMT-on product from the shorter DMT-off failure sequences. The efficiency was due to the large difference in hydrophobicity exhibited by the fill-length DMT-on product and the shorter DMT-off failure sequences. The RP-HPLC step was performed using a Waters HC-C18 HA "Bonda-Pak" octadecylsilyl silica (37–55 μm, 125 Å) radial compression column, selected for its flow characteristics, efficiency, durability and high loading capacity. The radial compression column was equilibrated with a mixture of water/methanol/ 2.5 M sodium acetate using a Biotage Kiloprep 100 HPLC system.

A solution of crude Oligonucleotide 6 (ISIS 104838) in the starting solvent mixture was loaded onto the column and the column eluted with an increasing step gradient of methanol in sodium acetate buffer (pH 7.2). The elution profile was monitored by continuous UV absorption spectrophotometry. The DMT-on product peak was collected in fractions and analyzed. The fractions that meet specification were pooled together and analyzed for %-area full-length. The RP-HPLC eluate containing the main product was transferred to a precipitation tank and dissolved in 0.01 M sodium acetate (pH 3). The pH of the resulting solution was determined and based on the determination, the requisite detritylation time was calculated. After incubation at room temperature for the prescribed time, the detritylated oligonucleotide was precipitated and the resulting precipitate isolated. Oligonucleotides 1–5, 7, and 8 were prepared in an analogous manner.

In an alternative method for preparing a purified oligonucleotide, the required quantity of room-temperature ethanol was calculated and transferred to the precipitation tank and agitation was begun. Trityl eluate material from reverse-phase HPLC purification was transferred to the ethanol in the precipitation tank. This precipitated the oligonucleotide, and allowed the unwanted HPLC mobile-phase components (e.g., methanol and salts) to be skimmed into the waste stream during centrifugation. A low-speed centrifugation was started at a speed of about 3000 RPM, and a peristaltic pump was used at a flow rate of 3000 ml/minute or less to pump the precipitated oligonucleotide into the centrifuge. Because of centrifugal force, the oligonucleotide adhered to the surfaces of the bowl, while the liquid was skimmed off and directed to the waste stream. Following completion of centrifugation, the precipitated oligonucleotide in the centrifuge bowl was dried using an argon gas flow. The oligonucleotide was reconstituted in the bowl by adding a calculated amount of water and adjusting the centrifuge RPMs to maximize contact of water with the oligonucleotide cake. The reconstituted material was transferred back to the precipitation tank for the detritylation reaction.

A calculated amount of the acidifying solution, 0.01 M NaOAc, (pH=2.9 to 3.1) was added to the tank containing the oligonucleotide solution, and the reaction was allowed to proceed for a calculated time interval based on a measured pH. The detritylation reaction was stopped by adding a calculated amount of 3.0 M NaOAc (pH 8.0).

Next, a calculated amount of room-temperature ethanol was added, which precipitated the oligonucleotide, but allowed the now-cleaved 5'-dimethoxytrityl group to stay in solution, where it was directed to the waste stream. Centrifuge was performed at a speed of about 3000 RPM and a peristaltic pump was used at a flow rate at 3000 ml/minute or less to pump the precipitated oligonucleotide into the centrifuge. Following completion of centrifugation, the oligonucleotide was reconstituted in the bowl by adding a calculated amount of water and adjusting the centrifuge RPMs to maximize contact of water with the oligonucleotide cake.

The reconstituted material was transferred to an appropriately-sized vessel, where the pH of the reconstituted material was adjusted to 7.2–7.5 with glacial acetic acid and/or 1.0 N NaOH. A calculated amount of 3.0M NaOAc solution was added to the pH-adjusted oligonucleotide solution. A calculated amount of room-temperature ethanol was added to the precipitation tank. The detritylated solution/NaOAc mixture was then added to the ethanol, which precipitated the oligonucleotide and allowed the salt that was generated during the pH-adjustment step to stay in solution, where it was directed to the waste stream.

The centrifuge was started at a speed of about 3000 RPM and a peristaltic pump was used at a flow rate of 3000 ml/minute or less to pump the precipitated oligonucleotide into the centrifuge. Following completion of centrifugation, the precipitated oligonucleotide in the centrifuge bowl was dried using an argon gas flow. The oligonucleotide was reconstituted in the bowl by adding a calculated amount of water and adjusting the centrifuge RPMs to maximize contact of water with the oligonucleotide cake. The reconstituted material was transferred to an appropriate vessel for filtration and lyophilization.

The oligonucleotides were isolated by gravitational settling, centrifugation or filtration. Bench top gravitational settling was performed using 10 mL and 50 mL conical centrifuge tubes. Small-scale, spin-tube experiments were performed in a Sorvall® fixed angle rotor centrifuge (E. I. DuPont de Nemours & Company fitted with a SLA 3000 rotor, capable of accommodating 10 and 25 mL centrifuge tubes. Additional data was produced using a Carr Powerfuge Pilot, with a maximum capacity of 250 g. A small scale Robatel, Slab 320 sedimenting centrifuge with a 20 Kg capacity was used to demonstrate scalability. Vacuum filtration experiments were conducted in 43 mm, 100 mm and 213 mm Buchner funnels, fitted with either a 10 µm or 20 µm, 316 stainless steel filter. Larger filtration experiments utilized a Pharmacia fine line 350 column, fitted with a 10 µm bottom frit. A ⅛ hp Gast vacuum pump was used to aid flow during the filtration.

Drying experiments were performed in one of the following: a NAPCO vacuum oven, Leybold lyophilizer, LabLine oven or a custom designed water-jacketed vacuum filter fitted with a gas inlet. Dried powders were analyzed for residual ethanol content by gas chromatography.

The percentage of oligonucleotide in solution was determined by ultraviolet (U.V.) spectrophotometer. The term "OD," as used herein, refers to absorbency at 260 nanometers using a 1 cm path length. The percentage of suspended solids or oligonucleotide remaining in the liquid phase according to the particular test parameters gauged the effectiveness of the stressed factor. Variables that resulted in low levels of product remaining in solution were considered effective.

Example 1

The Influence of Solvent Temperature on Precipitation of Full-Length, Dimethoxytrityl (DMT) Protected Fractions 3 mL of Oligonucleotide No. 2 <SEQ. ID NO:2> (ISIS 2302) having an initial concentration of 1263 OD/mL, was precipitated into 3 volumes of either cold (−20° C.) or ambient temperature (18–20° C.) ethanol, 1-propanol, isopropanol, or denatured ethanol (Solvent). The resulting mixture was briefly agitated and then followed by either gravitational settling for 1.5 hours or centrifugation at a speed of 2,000 RPM for 2 minutes. An aliquot (1 mL) of the liquid phase was then analyzed for concentration of oligonucleotide in the liquid phase using an ultraviolet (UV) spectrophotometer. The percentage of oligonucleotide remaining in the liquid phase (% Oligo in Liquid Phase) was determined. The results of treatment with cold and ambient temperature solvent followed by gravitational settling and low speed centrifugation are shown in Tables 2 and 3, respectively.

TABLE 2

| Temperature | Solvent | Initial Conc. (OD/mL) | Conc. in Liquid Phase (OD/mL) | % Oligo in Liquid Phase |
|---|---|---|---|---|
| −20° C. | Ethanol | 1263 | 60.6 | 4.8 |
| Ambient | Ethanol | 1263 | 3.7 | 0.29 |
| −20° C. | 1-Propanol | 1263 | 65.7 | 5.2 |
| Ambient | 1-Propanol | 1263 | 3.9 | 0.31 |
| −20 | IPA | 1263 | 61.2 | 4.9 |
| Ambient | IPA | 1263 | 3.2 | 0.25 |
| −20 | Denatured Ethanol | 1263 | 68.2 | 5.4 |
| Ambient | Denatured Ethanol | 1263 | 3.9 | 0.31 |

TABLE 3

| Temperature | Solvent | Initial Concentr. (OD/mL) | Concentr. in Liquid Phase (OD/mL) | % Oligo in Liquid Phase |
|---|---|---|---|---|
| −20° C. | Ethanol | 2118 | 59.3 | 2.8 |
| Ambient | Ethanol | 2118 | 4.7 | 0.22 |
| −20° C. | 1-Propanol | 2118 | 69.9 | 3.3 |
| Ambient | 1-Propanol | 2118 | 4.7 | 0.22 |
| −20 | IPA | 2118 | 89 | 4.2 |
| Ambient | IPA | 2118 | 4.0 | 0.19 |
| −20 | Denatured Ethanol | 2118 | 93.2 | 4.4 |
| Ambient | Denatured Ethanol | 2118 | 5.5 | 0.26 |

The data of Table 2 show that, when cold solvents were used, the total dissolved oligonucleotide remaining in the solution phase was between 4.8 and 5.4%. Upon inspection, the oligonucleotides treated with cold solvents were observed to produce an evenly dispersed fine precipitate, which remained suspended in the liquid phase and did not settle out of the solvent after 1.5 hours. In contrast, ambient temperature solvents immediately produced large aggregates that quickly settled, leaving the liquid phase clear. Product retention in the supernatant of the ambient temperature treated oligonucleotides was between 0.25 and 0.31%, for each solvent tested.

The data of Table 3 similarly show that 2.8–4.4% of suspended solid remained in the liquid phase of the slurries produced by cold temperature precipitation, while less than 0.3% of the product remained when using ambient temperature alcohol. Similar results were obtained in parallel experiments in which identical quantities of Oligonucleotide No. 4 <SEQ. ID NO.4> (ISIS 2503) were precipitated in either cold or room-temperature ethanol and then centrifuged at a slow speed (2000 RPM), or isolated by sedimentation.

Example 2

The Influence of Solvent Ratio on the Precipitation of DMT-Protected Full-Length Fractions 3 mL aliquots of DMT protected Oligonucleotide No. 4 <SEQ. ID NO:4> (ISIS 2503) having an initial concentration of 1785 OD/mL were precipitated in 1–4.5 volumes of ambient temperature ethanol. The resulting mixture was briefly agitated for 1 minute and then allowed to settle for 1.5 hours. After settling, approximately 1 mL of the solution phase was collected and the concentration and percentage of oligonucleotide remaining in the liquid phase (% Oligo in Liquid Phase) was determined. The results are presented in Table 4.

TABLE 4

| Oligonucletide: Solvent Ratio | Solvent | Initial Conc. (OD/mL) | Conc. In Liquid Phase (OD/mL) | % Oligo in Liquid Phase |
|---|---|---|---|---|
| 1:1 | Ethanol | 1785 | — | — |
| 1:1.5 | Ethanol | 1785 | — | — |
| 1:2 | Ethanol | 1785 | 8.9 | 0.5 |
| 1:2.5 | Ethanol | 1785 | 10.4 | 0.58 |
| 1:3 | Ethanol | 1785 | 8.9 | 0.5 |
| 1:3.5 | Ethanol | 1785 | 10.4 | 0.58 |
| 1:4 | Ethanol | 1785 | 12.0 | 0.67 |
| 1:4.5 | Ethanol | 1785 | 12.0 | 0.67 |
| 1:5 | Ethanol | 1785 | 13.6 | 0.76 |
| 1:3 | 1-Propanol | 1785 | 10.4 | 0.58 |
| 1:3 | IPA | 1785 | 8.9 | 0.5 |
| 1:3 | Denatured Ethanol | 1785 | 12.0 | 0.67 |

The data of Table 4 show that solution phase oligonucleotide content for ethanol volumes of 2.5 times to 3.5 times the volume of oligonucleotide was less than 0.58%. Ethanol volumes of 4 times, 4.5 times and 5 times the volume of the oligonucleotide had no significant additional effect on precipitation, although a slight increase of product remaining in the liquid phase was noted. When using 1-propanol and IPA the results were almost identical to those observed with ethanol. The results with denatured alcohol indicated a slight increase in the percent of oligonucleotide in the liquid phase. Further, it was observed that ethanol volumes of 1 and 1.5 times were not sufficient to induce complete precipitation, whereas an ethanol volume of 2 times the volume of oligonucleotide produced large aggregates which immediately began settling. However, the aggregates quickly became gelatinous and could not be resuspended by agitation. No distinctions were observed between precipitations induced by volumes of 2.5 times to 3.5 times the volume of oligonucleotide. In addition, aggregates formed during settling were easily resuspended by gentle agitation.

The aforementioned protocol was repeated except that the slurries were quickly transferred to the Sorvall® centrifuge and centrifuged at 2,000 RPM for 2 minutes. The amount of oligonucleotide remaining in the liquid phase (% Oligo in Liquid Phase) following centrifugation was determined and is shown in Table 5.

TABLE 5

| Oligonucletide: Solvent Ratio | Solvent | Initial Conc. (OD/mL) | Conc. In Liquid Phase (OD/mL) | % Oligo in Liquid Phase |
|---|---|---|---|---|
| 1:1 | Ethanol | 1785 | — | — |
| 1:1.5 | Ethanol | 1785 | — | — |
| 1:2 | Ethanol | 1785 | 5.0 | 0.28 |
| 1:2.5 | Ethanol | 1785 | 3.9 | 0.22 |
| 1:3 | Ethanol | 1785 | 3.2 | 0.18 |
| 1:3.5 | Ethanol | 1785 | 4.6 | 0.26 |
| 1:4 | Ethanol | 1785 | 4.1 | 0.23 |

TABLE 5-continued

| Oligonucletide: Solvent Ratio | Solvent | Initial Conc. (OD/mL) | Conc. In Liquid Phase (OD/mL) | % Oligo in Liquid Phase |
|---|---|---|---|---|
| 1:4.5 | Ethanol | 1785 | 9.8 | 0.55 |
| 1:5 | Ethanol | 1785 | 11.6 | 0.65 |
| 1:3 | 1-Propanol | 1785 | 4.3 | 0.24 |
| 1:3 | IPA | 1785 | 3.6 | 0.20 |

TABLE 6

| SEQ. ID NO. | ISIS # | Initial Conc. (OD/mL) | Solvent | Nature of Sediment | Filterability* | % Oligo in Liquid Phase |
|---|---|---|---|---|---|---|
| 4 | CA2503-007 G1 | 291 | Ethanol | Sticky | A | — |
| 4 | CA2503-007 G2 | 344 | Ethanol | Soft | A | — |
| 4 | CA2503-007 G4 | 365 | Ethanol | Soft | A | — |
| 4 | CA2503-007 G6 | 392 | Ethanol | Soft | A | — |
| 4 | CA2503-007 G7 | 426 | Ethanol | Soft | A | — |
| 4 | CA2503-007 G9 | 689 | Ethanol | Granular | C | 0.3 |
| 2 | CA2302-018 G10 | 706 | Ethanol | Semi-brittle | D | 0.2 |
| 2 | CA2302-018 G11 | 573 | Ethanol | Granular | B | 0.5 |
| 2 | CA2302-018 G12 | 733 | Ethanol | Brittle | B | 0.3 |
| 2 | CA2302-018 G13 | 888 | Ethanol | Brittle | D | 0.2 |
| 2 | CA2302-018 G14 | 384 | Ethanol | Soft | A | — |
| 2 | CA2302-018 G15 | 620 | Ethanol | Brittle | C | 0.4 |
| 2 | CA2302-018 G17 | 561 | Ethanol | Granular | B | 0.5 |
| 2 | CA2302-018 G13 | 888 | 1-Propanol | Brittle | D | 0.3 |
| 4 | CA2503-007 G9 | 689 | IPA | Semi-brittle | C | 0.2 |
| 4 | CA2503-007 G9 | 689 | Denatured Ethanol | Semi-brittle | C | 0.3 |

*A = Filtration could not be achieved. B = Partial filtration achieved. C = Product retained on filter. D = Product retained on filter with excellent flow rate.

TABLE 5-continued

| Oligonucletide: Solvent Ratio | Solvent | Initial Conc. (OD/mL) | Conc. In Liquid Phase (OD/mL) | % Oligo in Liquid Phase |
|---|---|---|---|---|
| 1:3 | Denatured Ethanol | 1785 | 3.4 | 0.19 |

The data of Table 5 show that there was no significant benefit to using ethanol volumes in excess of about 2.5 times the volume of oligonucleotide. In fact, there was a slight increase in the amount of oligonucleotide remaining in solution after treating with volumes in excess of about 4.5 times the volume of oligonucleotide, following centrifugation. When using 1-propanol, IPA and denatured alcohol, the results were slightly improved compared to those produced using ethanol.

Example 3

Effects of DMT-Protected Full length Oligonucleotide Concentration on Precipitation and Filtration A small volume of DMT-protected oligonucleotide was retained from the production of Oligonucletide Nos. 2 and 4 <SEQ. ID NO:2; SEQ. ID NO:4> (ISIS 2302; ISIS 2503) and tested as follows: 3 mL of oligonucleotide was precipitated in 3 volumes of ambient temperature ethanol while stirring for 1 minute. The nature of the slurry was determined by visual inspection and the resulting slurry was filtered through a small Buchner funnel, fitted with a 5.5 cm, Whatman No. 4 filter under vacuum. The slurry was given a rating (A–D) on its filterability. Assuming the slurry produced was capable of being retained on the filter, a small volume of the filtrate was collected and the percentage of oligonucleotide remaining in the liquid phase (% Oligo in Liquid Phase) was determined. The results are presented in Table 6.

DMT-protected eluate concentrations of 291, 344, 365, 384, 392 and 426 OD/mL produced large aggregates during precipitation. However, the aggregates formed a soft gelatinous film across the filter membrane surface making filtration impossible. DMT-protected eluate concentrations of 561, 573 and 689 OD/mL produced semi-hard granular aggregates upon precipitation, which filtered rather slowly. As the eluate concentration increased to 706 OD/mL and above, the aggregates became dry and brittle. Filtration flow rate indicated that these brittle aggregates could easily be separated from the liquid phase. Analysis indicated that less than 0.3% of the product remained in the filtrate waste. Procedures using ambient temperature 1-propanol, IPA and denatured ethanol demonstrated similar results to those obtained with ethanol.

Example 4

The Effects of Solvent Temperature on Precipitation of Full-Length DMT-Off Oligonucleotides Detritylated full-length Oligonucleotide Nos. 1 and 2 <SEQ. ID NO.: 1; SEQ. ID NO:2> (ISIS 5132 and ISIS 2302) (25 mL) were precipitated in 3 volumes of ethanol, 1-propanol, IPA and denatured alcohol at −20° C. and ambient temperature (18–20° C.). The resulting slurry was then briefly agitated and allowed to settle for 1.5 hours. After completion of the settling period, a 1 mL aliquot of the solution phase was extracted and the percentage of oligonucleotide remaining in the liquid phase (% Oligo in Liquid Phase) was determined. The results are presented in Table 7.

TABLE 7

| SEQ. ID NO. | ISIS # | Solvent | Temperature | Initial Conc. (OD/mL) | Conc. in Liquid Phase (OD/mL) | % Oligo in Liquid Phase |
|---|---|---|---|---|---|---|
| 1 | RA5132-013 | Ethanol | −20° C. | 54,380 | 2,400 | 4.2 |
| 2 | CA2302-018 | Ethanol | −20° C. | 55,220 | 2,800 | 5.0 |
| 1 | RA5132-013 | Ethanol | Ambient | 54,380 | 178 | 0.32 |
| 2 | CA2302-018 | Ethanol | Ambient | 55,220 | 185 | 0.33 |
| 1 | RA5132-018 | 1-Propanol | −20° C. | 54,380 | 2,920 | 5.4 |
| 2 | CA2302-018 | 1-Propanol | −20° C. | 55,220 | 3,229 | 5.8 |
| 1 | RA5132-013 | 1-Propanol | Ambient | 54,380 | 165 | 0.3 |
| 2 | CA2302-018 | 1-Propanol | Ambient | 55,220 | 142 | 0.26 |
| 1 | RA5132-013 | IPA | −20° C. | 54,380 | 2,990 | 5.5 |
| 2 | CA2302-018 | IPA | −20° C. | 55,220 | 2,650 | 4.8 |
| 1 | RA5132-013 | IPA | Ambient | 54,380 | 154 | 0.28 |
| 2 | CA2302-018 | IPA | Ambient | 55,220 | 144 | 0.26 |
| 1 | RA5132-013 | Denatured Ethanol | −20° C. | 54,380 | 2,770 | 5.1 |
| 2 | CA2302-018 | Denatured Ethanol | −20° C. | 55,220 | 2,985 | 5.4 |
| 1 | RA5132-013 | Denatured Ethanol | Ambient | 54,380 | 156 | 0.29 |
| 2 | CA2302-018 | Denatured Ethanol | Ambient | 55,220 | 177 | 0.32 |

The data in Table 7 show that the results were consistent when each of the alcohols was used. Cold temperature precipitation produced very fine, evenly dispersed granules, 4.2–5.8% of which remained in the solution phase after settling. Ambient temperature precipitation, however, immediately produced large aggregates which quickly settled, with, between 0.26 and 0.33% of product remaining in the solution phase following the settling period. This corresponds to a 90% reduction in product lost when using ambient temperature solvent.

The aforementioned protocol was repeated except that after precipitation, the tubes were centrifuged at 2,000 rpm for 2 minutes. The percentage of oligonucleotide remaining in the liquid phase (% Oligo in Liquid Phase) was determined. The results are presented in Table 8.

The data in Table 8 show that precipitation performed with solvent at a temperature of −20° C. resulted in 2.8–4.0% of oligonucleotide remaining in the liquid phase. When precipitation was performed with ambient temperature (18–21°) solvent, 0.21–0.25% of the product remained in the liquid phase.

Example 5

The Effects of Solvent Ratio on the Precipitation of Full-length DMT-Off Oligonucleotides Two oligonucleotides, Oligonucleotide Nos. 1 and 2 <SEQ. ID NO: 1; SEQ. ID NO:2> (ISIS 5132 and ISIS 2302) (25 mL) were precipitated in 1 to 5 volumes of ethanol, 1-propanol, IPA or denatured ethanol, vortexed for 25 seconds and allowed to settle for 1.5 hours. After settling, a 1 mL sample was collected and the percentage of oligo-

TABLE 8

| SEQ. ID NO. | ISIS # | Solvent | Temperature | Initial Conc. (OD/mL) | Conc. in Liquid Phase (OD/mL) | % Oligo in Liquid Phase |
|---|---|---|---|---|---|---|
| 1 | RA5132-013 | Ethanol | −20° C. | 54,380 | 1,950 | 3.5 |
| 2 | CA2302-018 | Ethanol | −20° C. | 55,220 | 1,600 | 2.8 |
| 1 | RA5132-013 | Ethanol | Ambient | 54,380 | 140 | 0.25 |
| 2 | CA2302-018 | Ethanol | Ambient | 55,220 | 133 | 0.24 |
| 1 | RA5132-018 | 1-Propanol | −20° C. | 54,380 | 2,200 | 4.0 |
| 2 | CA2302-018 | 1-Propanol | −20° C. | 55,220 | 1,955 | 3.5 |
| 1 | RA5132-013 | 1-Propanol | Ambient | 54,380 | 122 | 0.22 |
| 2 | CA2302-018 | 1-Propanol | Ambient | 55,220 | 133 | 0.24 |
| 1 | RA5132-013 | IPA | −20° C. | 54,380 | 2,019 | 3.7 |
| 2 | CA2302-018 | IPA | −20° C. | 55,220 | 2,215 | 4.0 |
| 1 | RA5132-013 | IPA | Ambient | 54,380 | 126 | 0.24 |
| 2 | CA2302-018 | IPA | Ambient | 55,220 | 128 | 0.23 |
| 1 | RA5132-013 | Denatured Ethanol | −20° C. | 54,380 | 2,010 | 3.6 |
| 2 | CA2302-018 | Denatured Ethanol | −20° C. | 55,220 | 1,966 | 3.6 |
| 1 | RA5132-013 | Denatured Ethanol | Ambient | 54,380 | 127 | 0.23 |
| 2 | CA2302-018 | Denatured Ethanol | Ambient | 55,220 | 118 | 0.21 | nucleotide present in the liquid phase was determined. The results are presented in Table 9.

TABLE 9

| SEQ. ID NO | ISIS # | Solvent | Oligonucleotide: Solvent Ratio | Initial Conc. (OD/mL) | Conc. in Liquid Phase (OD/mL) | % Oligo in Liquid Phase |
|---|---|---|---|---|---|---|
| 1 | RA5132-013 | Ethanol | 1:1 | 54,380 | NA | — |
| 2 | CA2302-018 | Ethanol | 1:1 | 55,220 | NA | — |
| 1 | RA5132-013 | Ethanol | 1:1.5 | 54,380 | NA | — |
| 2 | CA2302-018 | Ethanol | 1:1.5 | 55,220 | NA | — |
| 1 | RA5132-013 | Ethanol | 1:2 | 54,380 | 420 | 0.77 |
| 2 | CA2302-018 | Ethanol | 1:2 | 55,220 | 380 | 0.69 |
| 1 | RA5132-013 | Ethanol | 1:2.5 | 54,380 | 155 | 0.28 |
| 2 | CA2302-018 | Ethanol | 1:2.5 | 55,220 | 220 | 0.39 |
| 1 | RA5132-013 | Ethanol | 1:3 | 54,380 | 166 | 0.31 |
| 2 | CA2302-018 | Ethanol | 1:3 | 55,220 | 176 | 0.32 |
| 1 | RA5132-013 | Ethanol | 1:3.5 | 54,380 | 182 | 0.34 |
| 2 | CA2302-018 | Ethanol | 1:3.5 | 55,220 | 188 | 0.34 |
| 1 | RA5132-013 | Ethanol | 1:4 | 54,380 | 199 | 0.36 |
| 2 | CA2302-018 | Ethanol | 1:4 | 55,220 | 215 | 0.39 |
| 1 | RA5132-013 | Ethanol | 1:4.5 | 54,380 | 200 | 0.38 |
| 2 | CA2302-018 | Ethanol | 1:4.5 | 55,220 | 218 | 0.39 |
| 1 | RA5132-013 | Ethanol | 1:5 | 54,380 | 288 | 0.53 |
| 2 | CA2302-018 | Ethanol | 1:5 | 55,220 | 312 | 0.57 |
| 1 | CA2302-018 | 1-Propanol | 1:3 | 55,220 | 177 | 0.32 |
| 2 | RA5132-013 | 1-Propanol | 1:3 | 54,380 | 163 | 0.3 |
| 1 | CA2302-018 | IPA | 1:3 | 55,220 | 152 | 0.28 |
| 2 | RA5132-013 | IPA | 1:3 | 54,380 | 162 | 0.3 |
| 1 | CA2302-018 | Denatured Ethanol | 1:3 | 55,220 | 166 | 0.3 |
| 2 | RA5132-013 | Denatured Ethanol | 1:3 | 54,380 | 171 | 0.31 |

It was observed that ethanol volumes of 1 and 1.5 times were not sufficient to induce complete precipitation. Volumes of 2 times produced large aggregates that quickly settled, forming a sticky coating on the bottom of the centrifuge tube. Aggregates produced by 2.5 times, 3 times and 3.5 times the volume of oligonucleotide produced no observable distinctions. The product remaining in the solution phase was determined to be less than about 0.39%. Volumes of 4 times, 4.5 times and 5 times produced large aggregates but, there was a slight increase in the amount of oligonucleotide (greater than about 0.39%) remaining in the liquid phase after settling. Consequently, volumes of ethanol greater than about 2.5 times the volume of olignucleotide did not appear to improve product recovery.

The aforementioned protocol was repeated except that the slurries were subjected to centrifugation at 2,000 rpm for 1 minute. The percentage of oligonucleotide remaining in the liquid phase was determined and the results presented in Table 10.

TABLE 10

| SEQ. ID NO | ISIS # | Solvent | Oligonucleotide: Solvent Ratio | Initial Conc. (OD/mL) | Conc. in Liquid Phase (OD/mL) | % Oligo in Liquid Phase |
|---|---|---|---|---|---|---|
| 1 | RA5132-013 | Ethanol | 1:1 | 54,380 | NA | — |
| 2 | CA2302-018 | Ethanol | 1:1 | 55,220 | NA | — |
| 1 | RA5132-013 | Ethanol | 1:1.5 | 54,380 | NA | — |
| 2 | CA2302-018 | Ethanol | 1:1.5 | 55,220 | NA | — |
| 1 | RA5132-013 | Ethanol | 1:2 | 54,380 | 111 | 0.20 |
| 2 | CA2302-018 | Ethanol | 1:2 | 55,220 | 122 | 0.22 |
| 1 | RA5132-013 | Ethanol | 1:2.5 | 54,380 | 144 | 0.26 |
| 2 | CA2302-018 | Ethanol | 1:2.5 | 55,220 | 195 | 0.35 |
| 1 | RA5132-013 | Ethanol | 1:3 | 54,380 | 161 | 0.31 |
| 2 | CA2302-018 | Ethanol | 1:3 | 55,220 | 121 | 0.22 |
| 1 | RA5132-013 | Ethanol | 1:3.5 | 54,380 | 189 | 0.34 |
| 2 | CA2302-018 | Ethanol | 1:3.5 | 55,220 | 188 | 0.34 |
| 1 | RA5132-013 | Ethanol | 1:4 | 54,380 | 255 | 0.46 |
| 2 | CA2302-018 | Ethanol | 1:4 | 55,220 | 235 | 0.42 |
| 1 | RA5132-013 | Ethanol | 1:4.5 | 54,380 | 305 | 0.56 |
| 2 | CA2302-018 | Ethanol | 1:4.5 | 55,220 | 325 | 0.58 |
| 1 | RA5132-013 | Ethanol | 1:5 | 54,380 | 355 | 0.65 |
| 2 | CA2302-018 | Ethanol | 1:5 | 55,220 | 388 | 0.70 |
| 1 | CA2302-018 | 1-Propanol | 1:3 | 55,220 | 115 | 0.21 |
| 2 | RA5132-013 | 1-Propanol | 1:3 | 54,380 | 122 | 0.22 |
| 1 | CA2302-018 | IPA | 1:3 | 55,220 | 119 | 0.21 |

TABLE 10-continued

| SEQ. ID NO | ISIS # | Solvent | Oligonucleotide: Solvent Ratio | Initial Conc. (OD/mL) | Conc. in Liquid Phase (OD/mL) | % Oligo in Liquid Phase |
|---|---|---|---|---|---|---|
| 2 | RA5132-013 | IPA | 1:3 | 54,380 | 133 | 0.24 |
| 1 | CA2302-018 | Denatured Ethanol | 1:3 | 55,220 | 126 | 0.23 |
| 2 | RA5132-013 | Denatured Ethanol | 1:3 | 54,380 | 116 | 0.21 |

The data in Table 10 show that alcohol volumes of 2.5 times, 3 times, and 3.5 times the volume of oligonucleotide produced results that were similar to those observed after settling. In particular, at those oligonucleotide to solvent ratios, less than 0.35% of oligonucleotide remained in the liquid phase. As the relative proportion of solvent increased from 4 times to 5 times, the percentage of oligonucleotide remaining in the liquid phase increased from 0.46 to 0.70%. It was observed, however, that precipitants formed using 2.5–3.5 volumes of solvent per volume oligonucleotide appeared slightly gelatinous.

Example 6

Effects of Order of Addition

The order of addition for the three precipitation components (e.g. alcohol, DMT-off oligonucleotide and sodium acetate) was varied. The resulting slurries were then allowed to settle for 1.5 hours at which point 1 mL samples of the solution phase were collected in order to determine the percentage of oligonucleotide remaining in the liquid phase (% Oligo in Liquid Phase). The results are presented in Table 11.

Following Procedure A, 145 μL of 3.0M NaOAc was added to 25 mL of DMT-off Oligonucleotide Nos. 1 or 2 <SEQ. ID NO: 1; SEQ. ID NO:2> (ISIS 5132; ISIS 2302), having a concentration of 2750 OD/mL. The resulting salt/oligonucleotide mixture was then added to three volumes of ethanol, 1-propanol, IPA or denatured ethanol and mixed for 30 seconds. The resulting slurry was allowed to settle for 1.5 hours and a 1 mL sample of the solution phase was collected to determine the concentration of oligonucleotide in the liquid phase (% Oligo in Liquid Phase). It was observed that large aggregates formed and immediately began to settle upon addition of the salt/oligonucleotide mixture to any of the alcohols used. The data in Table 11 show that less than about 0.35% of the oligonucleotide remained in the liquid phase after settling.

Procedure B involved transferring 145 μL of NaOAc to 75 mL ethanol, 1-propanol, IPA or denatured ethanol and mixing for 2 minutes. To this mixture, 25 mL oligonucleotide solution was added and the resulting slurry was mixed for 30 seconds. The mixture was then allowed to settle for 1.5 hours and a 1 mL sample of the solution phase was collected to determine the concentration of oligonucleotide in the liquid phase. It was observed that the aggregates produced by this protocol appeared small and the solution phase remained hazy. The data in Table 11 show that 6.5–9.2% of oligonucleotide remained in the solution phase.

Following Procedure C, 25 mL of oligonucleotide solution was transferred to 75 mL of ethanol and mixed for 1 minute. To this mixture, 145 μL of 3.0M NaOAc was added and the resulting slurry mixed for 30 seconds. The slurry was then allowed to settle and sampled as previously described. This protocol resulted in a mixture of large and small aggregates, with the small aggregates remaining suspended after 1.5 hours. A sample of the solution phase was collected to determine the concentration of oligonucleotide in the liquid phase. The solution phase contained between 7.3 and 10.0% of product.

TABLE 11

| SEQ. ID NO. | ISIS # | Solvent | Order of Addition* | Initial Conc. (OD/mL) | Conc. in Liquid Phase (OD/mL) | % Oligo in Liquid Phase |
|---|---|---|---|---|---|---|
| 1 | RA5132-013 | Ethanol | A | 54,380 | 188 | 0.35 |
| 2 | CA2302-018 | Ethanol | A | 55,220 | 166 | 0.3 |
| 1 | RA5132-013 | 1-Popanol | A | 54,380 | 174 | 0.32 |
| 2 | CA2302-018 | 1-Popanol | A | 55,220 | 192 | 0.35 |
| 1 | RA5132-013 | IPA | A | 54,380 | 153 | 0.28 |
| 2 | CA2302-018 | IPA | A | 55,220 | 140 | 0.25 |
| 1 | RA5132-013 | Denatured Ethanol | A | 54,380 | 163 | 0.3 |
| 2 | CA2302-018 | Denatured Ethanol | A | 55,220 | 166 | 0.3 |
| 1 | RA5132-013 | Ethanol | B | 54,380 | 3,555 | 6.5 |
| 2 | CA2302-018 | Ethanol | B | 55,220 | 4,789 | 8.8 |
| 1 | RA5132-013 | 1-Propanol | B | 54,380 | 3,899 | 7.2 |
| 2 | CA2302-018 | 1-Propanol | B | 55,220 | 2,777 | 5.0 |
| 1 | RA5132-013 | IPA | B | 54,380 | 5,010 | 9.2 |
| 2 | CA2302-018 | IPA | B | 55,220 | 4,661 | 8.4 |
| 1 | RA5132-013 | Denatured Ethanol | B | 54,380 | 3,897 | 7.2 |

TABLE 11-continued

| SEQ. ID NO. | ISIS # | Solvent | Order of Addition* | Initial Conc. (OD/mL) | Conc. in Liquid Phase (OD/mL) | % Oligo in Liquid Phase |
|---|---|---|---|---|---|---|
| 2 | CA2302-018 | Denatured Ethanol | B | 55,220 | 3,775 | 6.9 |
| 1 | RA5132-013 | Ethanol | C | 54,380 | 5,521 | 10.0 |
| 2 | CA2302-018 | Ethanol | C | 55,220 | 5,630 | 10.0 |
| 1 | RA5132-013 | 1-Propanol | C | 54,380 | 4,878 | 8.9 |
| 2 | CA2302-018 | 1-Propanol | C | 55,220 | 5,218 | 9.4 |
| 1 | RA5132-013 | IPA | C | 54,380 | 3,945 | 7.3 |
| 2 | CA2302-018 | IPA | C | 55,220 | 4,231 | 7.7 |
| 1 | RA5132-013 | Denatured Ethanol | C | 54,380 | 4,966 | 9.1 |
| 2 | CA2302-018 | Denatured Ethanol | C | 55,220 | 4,555 | 8.2 |

*A = Oligo mixed with NaOAc and transferred to alcohol. B = Alcohol mixed with Oligo and NaOAc transferred to mixture; and C = Alcohol mixed with NaOAc and oligonucleotide transferred to mixture.

Example 7

The Effects of Full-Length, DMT-Off, Oligonucleotide Concentration on Aggregate Formation and Filtration Solutions containing oligonucleotide concentrations ranging from 1000 OD/mL to 4750 D/mL, were prepared using Oligonucleotide Nos. 1 or 5 <SEQ. ID NO: 1 or SEQ. ID NO:5> (ISIS 5132 or ISIS 3521) formed as lyophilized powders. To these stock solutions, 3.0 M NaOAc was added and the resulting mixture vortexed. The mixture was then precipitated in 3 volumes of ethanol and the resulting slurry was filtered through a Buchner funnel, fitted with a 5.5 cm Whatman No. 4 filter under vacuum. The slurry was given a rating (A-D) based on ease of filtration. The percentage of oligonucleotide remaining in the filtrate (% Oligo in Filtrate) was determined after filtration. The results of the filtration are presented in Table 12.

TABLE 12

| SEQ. ID NO. | ISIS # | Initial Conc. (OD/mL) | Conc. of Oligonucleotide in filtrate (OD/mL) | % of Oligo in Filtrate | Filtration* |
|---|---|---|---|---|---|
| 1 | RA5132-013 | 1,000 | — | — | A |
| 2 | CA2302-018 | 1,000 | — | — | A |
| 1 | RA5132-013 | 1,250 | — | — | A |
| 2 | CA2302-018 | 1,250 | — | — | A |
| 1 | RA5132-013 | 1,500 | — | — | A |
| 2 | CA2302-018 | 1,500 | — | — | A |
| 1 | RA5132-013 | 1,750 | — | — | A |
| 2 | CA2302-018 | 1,750 | — | — | A |
| 1 | RA5132-013 | 2,000 | — | — | A |
| 2 | CA2302-018 | 2,000 | — | — | A |
| 1 | RA5132-013 | 2,250 | 2,200 | 3.5 | B |
| 2 | CA2302-018 | 2,250 | 2,200 | 3.9 | B |
| 1 | RA5132-013 | 2,500 | 822 | 1.3 | B |
| 2 | CA2302-018 | 2,500 | 759 | 1.2 | B |
| 1 | RA5132-013 | 2,750 | 456 | 0.6 | C |
| 2 | CA2302-018 | 2,750 | 466 | 0.7 | C |
| 1 | RA5132-013 | 3,000 | 166 | 0.2 | D |
| 2 | CA2302-018 | 3,000 | 155 | 0.2 | D |
| 1 | RA5132-013 | 3,250 | 177 | 0.2 | D |
| 2 | CA2302-018 | 3,250 | 189 | 0.3 | D |
| 1 | RA5132-013 | 3,500 | 186 | 0.2 | D |
| 2 | CA2302-018 | 3,500 | 201 | 0.2 | D |
| 1 | RA5132-013 | 3,750 | 215 | 0.2 | D |
| 2 | CA2302-018 | 3,750 | 230 | 0.2 | D |
| 1 | RA5132-013 | 4,000 | 244 | 0.2 | D |
| 2 | CA2302-018 | 4,000 | 256 | 0.3 | D |
| 1 | RA5132-013 | 4,250 | 326 | 0.3 | D |
| 2 | CA2302-018 | 4,250 | 289 | 0.3 | D |
| 1 | RA5132-013 | 4,500 | 333 | 0.3 | D |
| 2 | CA2302-018 | 4,500 | 389 | 0.3 | D |
| 1 | RA5132-013 | 4,750 | 829 | 0.69 | B |
| 2 | CA2302-018 | 4,750 | 955 | 0.8 | B |

*A = Filtration could not be achieved. B = Partial filtration achieved; C = Product was retained on filter; and D = Product retained on filter and excellent flow rate.

It was observed that oligonucleotide concentrations ranging from 1000 to 2000 OD/mL produced large aggregates and that they formed a gelatinous layer. As a result, they could not be filtered. Initial oligonucleotide concentrations of 2,250 OD/mL could be partially filtered and 3.5–3.9% of the product remained in the liquid phase.

The data in Table 12 show that as the initial concentration of oligonucleotide increases from 2500 to 2750 OD/mL, the filtration rate improved considerably and the percentage of product remaining in the liquid phase was reduced to 0.6–1.3%. Optimal filtration was achieved by precipitating solutions with a concentration of oligonucleotide ranging from 3000 to 4500 OD/mL. Filtration of solutions containing these concentrations resulted in a reduction in the amount of product remaining in liquid phase to less than about 0.3%.

Example 8

Lots Produced Per the FDA's Good Manufacturing Practices Guidelines Using Room Temperature Ethanol Six lots of Oligonucleotide Nos. 3–7 <SEQ. ID NOS: 3–7> (ISIS 14803, ISIS 2503, ISIS 3521, ISIS 104838, and ISIS 107248) have been successfully processed using room temperature ethanol and the Carr centrifuge.

Example 9

Small Scale Slow Speed Centrifugation

Oligonucleotide Nos. 2 and 3 <SEQ. ID NOS 2, 3> (ISIS 2302, ISIS 14803) were processed in the Robatel Slab 320 sedimenting centrifuge, at 2,500 rpm. The results are presented in Table 13. The oligonucleotides were prepared following the previously described protocol.

TABLE 13

| SEQ. ID NO | ISIS # | Initial OD load | # of Precipitations | Post Centrifugation OD load | Total Yield |
|---|---|---|---|---|---|
| 2 | 2302 | 2,721,686 | 3 | 2,650,000 | 98.0% |
| 3 | RA 14803-006 | 342,814 | 3 | 312,500 | 91.2% |
| 1 | RA5132-013 | 9,375,000 | 1 | 9,365,625 | 99.9% |
| 2 | 2302 Short-mer | 27,500,000 | 1 | 27,431,250 | 99.75% |

The data of Table 13 show that good yields on a production scale can be obtained with slow-speed centrifugation.

Example 10

Small Scale Filtration and Drying

Several tests were conducted using DMT-off oligonucleotide solutions ranging from 50 g to 2.5 Kg. The procedure was as follows: 1) the final DMT-off oligonucleotide was reconstituted to form between 120 mg/mL to 150 mg/mL; 2) a 2% to 4% v/v 3.0 M NaOAc solution was added to the DMT-off oligonucleotide solution while stirring; 3) the resulting solution was transferred to 2.7–3.0 volumes of ambient temperature ethanol, with gentle agitation; 4) the slurry was transferred to a vacuum filter apparatus and filtered through a 10 or 20 µm 316ss filter; and 5) the cake was dried using oven, vacuum oven, vacuum, or filter drying. As detailed in Table 14, the resulting cake bed height ranged from a few millimeters to 11 centimeters. Yield data showed the loss of product ranged from 0.18 to 0.30%. The results are presented in Table 14.

TABLE 14

| SEQ. ID NO | ISIS # | Grams of Oligonucleotide | Filter Size (Microns) | Oligonucleotide Cake Bed Height (cm) | % Of Oligo in Effluent Waste |
|---|---|---|---|---|---|
| 2 | 2302 | 178 | 10 | 7.0 | 0.19 |
| 2 | 2302 | 203 | 20 | 7.5 | 0.21 |
| 2 | 2302 (side Fractions) | 47.5 | 10 | 4.0 | 0.26 |
| 2 | 2302 (Side Fractions) | 2,500 | 20 | 11.0 | 0.22 |
| 1 | 5132 | 250 | 10 | 8.9 | 0.30 |
| 1 | 5132 | 120 | 10 | 5.8 | 0.18 |
| 1 | 5132 | 180 | 20 | 6.2 | 0.24 |
| 3 | 14803 | 236 | 10 | 5.08 | 0.18 |

The results of these experiments are contained in Table 15. Precipitation and filtration steps were performed according to the protocol previously described.

TABLE 15

| SEQ. ID NO | ISIS # | Grams of Oligonucleotide | Drying Procedure | % Residual Ethanol | % Loss of Oligonucleotide |
|---|---|---|---|---|---|
| 2 | 2302 | 203 | Vacuum Oven | 0.32 | 0.2 |
| 2 | 2302 | 177 | Vacuum Tray | 0.56 | 0.0 |
| 1 | 5132 | 160 | Oven | 0.33 | 0.2 |
| 1 | 5132 | 120 | Vacuum Filter | — | 0.3 |

Vacuum Oven Drying

After collecting 203 g of Oligonucleotide No. 2 <SEQ. ID NO:2> (ISIS 2302) in a large Buchner funnel, the cake and funnel were transferred to a vacuum oven. The oven was then heated to 30° C. and 25 in/Hg vacuum pulled. After 25 hours, the dried cake was removed from the oven, passed through a #20 sifter screen, blended, weighed and sampled for residual ethanol testing.
Ethanol content of the final dried cake was 0.32%. The weight of the dried product was 202.6 g, indicating a product loss of less than 0.2%.

Vacuum Tray Drying

A wet cake, 177 g of Oligonucleotide No. 2 <SEQ. ID NO:2> (ISIS 2302), was collected in a large Buchner funnel, transferred to a 316ss lyophilization tray and quickly placed in the lyophilizer. The shelves were then heated to 30° C. and a vacuum pulled to 100 microns. After 24 hours of drying the product was passed through a #10 screen, blended and weighed. Ethanol content of the final dried product was 0.056%. The final weight of the dried material was 178 g, indicating that essentially no product was lost during processing.

Oven Drying 160 g of Oligonucleotide No. 1 <SEQ. ID NO:1> (ISIS 5132) mock-up solution was prepared, precipitated and collected in a Buchner funnel; the retained cake was quickly transferred to an oven that was preheated to 55° C. The cake was dried for 12 hours and then passed through a #20 sifter, weighed, blended. The final weight of the dried product was determined to be 159.6 g and had an ethanol content of 0.33%. This procedure resulted in approximately 0.2% loss of product.

Filter Vacuum Drying

A wet cake, 120 g, of Oligonucleotide No. 1 <SEQ. ID NO:1> (ISIS 5132) was collected by vacuum filtration, in a specially designed water-jacketed filter apparatus. Immediately following filtration, argon was purged through the cake while 30° C. water circulated through the jacket. After 15 hours of drying while purging with argon, the cake was passed through a number 20 sifter, blended and weighed. The final weight of the product was 119.5 g.

Example 11

Oligonucleotide-Specific Modifications

Product-specific reaction times (in minutes) required to reduce the 5'-dimethoxytrityl level by half have been calculated for the sequences listed below, where x=pH following acidification:

| | |
|---|---|
| 2302: | $t_{1/2} = 0.0148 * 10^{0.6773(x)}$ |
| 2503: | $t_{1/2} = 0.0031 * 10^{0.9235(x)}$ |
| 3521: | $t_{1/2} = 0.0074 * 10^{0.7195(x)}$ |
| 5132: | $t_{1/2} = 0.0147 * 10^{0.7696(x)}$ |
| 14803: | $t_{1/2} = 0.0103 * 10^{0.6554(x)}$ |
| 104838: | $t_{1/2} = 0.0072 * 10^{0.8093(x)}$ |
| 107248: | $t_{1/2} = 0.0200 * 10^{0.7516(x)}$ |

The number of minutes from the half-life calculation is then multiplied by 15, and the resulting number gives the total reaction time. By allowing the 5'-dimethoxytrityl level to be reduced by half for 15 iterations, the level detected is zero.

What is claimed is:

1. A method for preparing a purified oligonucleotide comprising the steps of:
    a) providing a solution comprising an oligonucleotide, said solution being effluent obtained from chromatography of crude oligonucleotide;
    b) treating said solution with an aggregating agent and a precipitation enhancer under conditions sufficient to form an oligonucleotide aggregate; and
    c) isolating said oligonucleotide aggregate to form said purified oligonucleotide.

2. The method of claim 1 wherein said solution comprises a deprotected oligonucleotide.

3. The method of claim 2 wherein said solution is acidic.

4. The method of claim 3 wherein said solution is prepared by treatment of a 5'-protected oligonucleotide in a solvent with a deprotecting agent effective to remove the 5'-protecting group.

5. The method of claim 4 wherein said 5'-protecting group is selected from the group consisting of trimethoxytrityl, dimethoxytrityl, monomethoxytrityl, 9-phenylxanthen-9-yl, and 9-(p-methoxyphenyl)xanthen-9-yl.

6. The method of claim 5 wherein said protecing group is dimethoxytrityl.

7. The method of claim 2 wherein the concentration of said deprotected oligonucleotide in said solution is at least about 2250 OD/mL.

8. The method of claim 7 wherein the concentration of said deprotected oligonucleotide in said solution is from about 2500 OD/mL to about 7500 OD/mL.

9. The method of claim 8 wherein the concentration of said deprotected oligonucleotide in said solution is from about 4500 OD/mL to about 6500 OD/mL.

10. The method of claim 1 wherein said solution is prepared by reconstituting an isolated, deprotected oligonucleotide in water.

11. The method of claim 1 wherein said aggregating agent comprises an alcohol.

12. The method of claim 11 wherein said alcohol is selected from the group consisting of methanol, ethanol, 1-propanol, isopropyl alcohol and denatured ethanol.

13. The method of claim 1 wherein said precipitation enhancer comprises a salt.

14. The method of claim 13 wherein said salt is selected from the group consisting of sodium salts, lithium salts, ammonium salts, potassium salts, magnesium salts, cesium salts and zinc salts.

15. The method of claim 14 wherein said salt is sodium acetate.

16. The method of claim 14 wherein said salt is sodium hydroxide.

17. The method of claim 1 wherein said oligonucleotide is treated with said aggregating agent at a temperature of between about 15° C. and about 25° C.

18. The method of claim 1 wherein said oligonucleotide is treated with said aggregating agent at a temperature from about 18° C. to about 20° C.

19. The method of claim 1 wherein said oligonucleotide is treated with said precipitation enhancer prior to treating said oligonucleotide with said aggregating agent.

20. The method of claim 1 wherein said oligonucleotide is treated with said aggregating agent prior to treating said oligonucleotide with said precipitation enhancer.

21. The method of claim 1 wherein said oligonucleotide is treated with a mixture of said precipitation enhancer and said aggregating agent.

22. The method of claim 1 wherein said solution is treated with said aggregating agent in a ratio of about 1 part solution to at least about 1.5 parts aggregating agent by volume.

23. The method of claim 22 wherein said solution is treated with said aggregating agent in a ratio of about 1 part solution to between about 2 parts and about 4 parts aggregating agent by volume.

24. The method of claim 22 wherein said solution is treated with said aggregating agent in a ratio of about 1 part solution to between about 2.5 parts and about 4.5 parts aggregating agent by volume.

25. The method of claim 1 wherein said oligonucleotide aggregate is isolated by centrifugation.

26. The method of claim 25 wherein said centrifugation is conducted at a speed of less than about 3000 rotations per minute.

27. The method of claim 26 wherein said centrifugation is conducted at a speed of less than about 2500 rotations per minute.

28. The method of claim 25 wherein said oligonucleotide is treated with said aggregating agent in a ratio of 1 part oligonucleotide to about 5 parts aggregating agent by volume.

29. The method of claim 28 wherein said aggregating agent is ethanol and said oligonucleotide is treated with said aggregating agent in a ratio of 1 part oligonucleotide to between about 2 and about 4 parts aggregating agent by volume.

30. The method of claim 29 wherein said aggregating agent is selected from the group consisting of 1-propanol, isopropyl alcohol and denatured ethanol and said oligonucleotide is treated with said aggregating agent in a ratio of 1 part oligonucleotide to about 3 parts aggregating agent by volume.

31. The method of claim 1 wherein said oligonucleotide is isolated by gravitational settling.

32. The method of claim 31 wherein said oligonucleotide is treated with said aggregating agent in a ratio of 1 part oligonucleotide to 5 parts aggregating agent by volume.

33. The method of claim 32 wherein said aggregating agent is ethanol and said oligonucleotide is treated with said aggregating agent in a ratio of 1 part oligonucleotide to between about 2 and about 4.5 parts aggregating agent by volume.

34. The method of claim 27 wherein said aggregating agent is ethanol and said oligonucleotide is treated with said aggregating agent in a ratio of 1 part oligonucleotide to between about 2 and about 3.5 parts aggregating agent by volume.

35. The method of claim 34 wherein said aggregating agent is selected from the group consisting of 1-propanol, isopropyl alcohol and denatured ethanol and said oligonucleotide is treated with said aggregating agent in a ratio of about 1 part oligonucleotide to about 3 parts aggregating agent by volume.

36. The method of claim 1 wherein said oligonucleotide is isolated by filtration.

37. The method of claim 36 wherein an amount of said oligonucleotide remaining in said solution after said oligonucleotide is isolated from said solution is not more than about 3.5%.

38. The method of claim 37 wherein an amount of said oligonucleotide remaining in said solution after said oligonucleotide is isolated from said solution is not more than about 1.5%.

39. The method of claim 38 wherein an amount of said oligonucleotide remaining in said solution after said oligonucleotide is isolated from said solution is not more than about 1%.

40. A method for preparing a purified oligonucleotide comprising the steps of:
    a) providing a solution comprising an oligonucleotide, said solution being effluent obtained from chromatography of crude oligonucleotide;
    b) treating said solution with ethanol, wherein said ethanol is at a temperature of between about 15° C. and about 25° C. and a sodium salt under conditions sufficient to form an oligonucleotide aggregate; and
    c) isolating said oligonucleotide aggregate to form said purified oligonucleotide.

41. The method of claim 40 wherein said sodium salt is sodium acetate or sodium hydroxide.

42. A method for preparing a purified oligonucleotide comprising the steps of:
    a) providing a solution comprising an oligonucleotide, said solution being effluent obtained from chromatography of crude oligonucleotide;
    b) treating said solution with a precipitation enhancer with subsequent treatment with an aggregating agent under conditions sufficient to form an oligonucleotide aggregate; and
    c) isolating said oligonucleotide aggregate to form said purified oligonucleotide.

43. The method of claim 42 wherein said precipitation enhancer is sodium acetate.

44. The method of claim 42 wherein said aggregating agent is selected from the group consisting of methanol, ethanol, 1-propanol, isopropyl alcohol and denatured ethanol.

45. A method for preparing a purified oligonucleotide comprising the steps of:
    treating a first solution comprising a 5'-protected oligonucleotide with an aggregating agent under conditions sufficient to form a first oligonucleotide aggregate;
    isolating said first oligonucleotide aggregate;
    dissolving the isolated first oligonucleotide aggregate in a solvent thereby forming a second solution;
    treating said second solution with a deprotecting reagent effective to remove said 5'-protecting groups;
    treating said second solution with an aggregating agent and a precipitation enhancer under conditions sufficient to form a second oligonucleotide aggregate;
    isolating said second oligonucleotide aggregate;
    dissolving said second oligonucleotide aggregate in a solvent to give a third solution; and
    treating said third solution with an aggregating agent and a precipitation enhancer under conditions sufficient to form a third oligonucleotide aggregate; and
    isolating said third oligonucleotide aggregate to give said purified oligonucleotide.

46. The method of claim 45 wherein said first solution is effluent obtained from chromatography of crude oligonucleotide.

47. The method of claim 46 wherein said chromatography is high pressure liquid chromatography.

48. The method of claim 47 wherein said high pressure liquid chromatography is performed using a column loaded with reverse phase media or strong anion exchange resin.

49. The method of claim 45 wherein said isolating of said first oligonucleotide aggregate or said second oligonucleotide aggregate is performed by gravitational settling or centrifugation.

50. The method of claim 45 wherein said isolating of said third oligonucleotide aggregate is performed by filtration.

51. The method of claim 45 wherein said purified oligonucleotide is at least about 90% pure.

52. The method of claim 51 wherein said purified oligonucleotide is at least about 98% pure.

53. A method for preparing a purified oligonucleotide comprising the steps of:
    treating a first solution comprising an oligonucleotide with an aggregating agent and a precipitation enhancer under conditions sufficient to form a first oligonucleotide aggregate;
    isolating said first oligonucleotide aggregate;
    dissolving the isolated first oligonucleotide aggregate in a solvent thereby forming a second solution;
    treating said second solution with an aggregating agent and a precipitation enhancer under conditions sufficient to form a second oligonucleotide aggregate; and
    isolating said second oligonucleotide aggregate to give said purified oligonucleotide.

54. The method of claim 53 wherein said purified oligonucleotide is at least about 90% pure.

55. The method of claim 54 wherein said purified oligonucleotide at least about 98% pure.

56. The method of claim 53 wherein said oligonucleotide of said first solution is a 5'-deprotected oligonucleotide.

57. The method of claim 56 wherein said first solution is prepared by acidification of HPLC effluent containing a 5'-protected oligonucleotide.

58. The method of claim 57 wherein said HPLC effluent results from HPLC purification of a cleaved and base deblocked 5'-protected oligonucleotide.

59. The method of claim 53 wherein said isolating of said first oligonucleotide aggregate is performed by gravitational settling or centrifugation.

60. The method of claim 53 wherein said isolating of said second oligonucleotide aggregate is performed by filtration.

61. The method of claim 49 wherein said solvent is water.

* * * * *

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide

<400> SEQUENCE: 1
tcccgcctgt gacatgcatt                                    20

```
<210> SEQ ID NO 2
<211> LENGTH: 20
<212> TYPE: DNA
<213> ORGANISM: Artificial Sequence
<220> FEATURE:
<223> OTHER INFORMATION: Oligonucleotide

<400> SEQUENCE: 2
gcccaagctg gcatccgtca                                              20

<210> SEQ ID NO 3
<211> LENGTH: 19
<212> TYPE: DNA
<213> ORGANISM: Artificial Sequence
<220> FEATURE:
<223> OTHER INFORMATION: Oligonucleotide

<400> SEQUENCE: 3
gtgctcatgg tgcacggtc                                               19

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide

<400> SEQUENCE: 4
tccgtcatcg ctcctcaggg                                              20

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide

<400> SEQUENCE: 5
gttctcgctg gtgagtttca                                              20

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide

<400> SEQUENCE: 6
gctgattaga gagaggtccc                                              20

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide

<400> SEQUENCE: 7
ctgagtctgt tttccattct                                              20

<210> SEQ ID NO 8
<211> LENGTH: 20
<212> TYPE: DNA
<213> ORGANISM: Artificial Sequence
<220> FEATURE:
```

-continued

<223> OTHER INFORMATION: Oligonucleotide

<400> SEQUENCE: 8
gctccttcca ctgatcctgc                    20